United States Patent
Jain et al.

(10) Patent No.: US 11,547,676 B2
(45) Date of Patent: Jan. 10, 2023

(54) EXTENDED BUPRENORPHINE TRANSDERMAL DELIVERY COMPOSITIONS AND METHODS FOR USING THE SAME

(71) Applicant: Teikoku Seiyaku Co., Ltd., Kagawa (JP)

(72) Inventors: Amit Jain, Milpitas, CA (US); Jianye Wen, Palo Alto, CA (US)

(73) Assignee: Teikoku Seiyaku Co., Ltd., Kagawa (JP)

(*) Notice: Subject to any disclaimer, the term of this patent is extended or adjusted under 35 U.S.C. 154(b) by 189 days.

(21) Appl. No.: 14/107,643

(22) Filed: Dec. 16, 2013

(65) Prior Publication Data

US 2014/0186421 A1    Jul. 3, 2014

Related U.S. Application Data

(60) Provisional application No. 61/746,832, filed on Dec. 28, 2012.

(51) Int. Cl.
*A61K 9/70* (2006.01)
*A61K 31/485* (2006.01)
*A61K 47/12* (2006.01)

(52) U.S. Cl.
CPC .......... *A61K 9/7061* (2013.01); *A61K 9/7053* (2013.01); *A61K 31/485* (2013.01); *A61K 47/12* (2013.01)

(58) Field of Classification Search
CPC .. A61K 31/485; A61K 9/7061; A61K 9/7053; A61K 47/12
See application file for complete search history.

(56) References Cited

U.S. PATENT DOCUMENTS

| | | |
|---|---|---|
| 4,806,341 A | 2/1989 | Chien et al. |
| 4,906,463 A | 3/1990 | Cleary et al. |
| 4,956,171 A | 9/1990 | Chang |
| 5,006,342 A | 4/1991 | Cleary et al. |
| 5,008,110 A | 4/1991 | Benecke et al. |
| 5,026,556 A | 6/1991 | Drust et al. |
| 5,069,909 A | 12/1991 | Sharma et al. |
| 5,091,186 A | 2/1992 | Miranda et al. |
| 5,132,115 A | 7/1992 | Wolter et al. |
| 5,149,538 A | 9/1992 | Granger et al. |
| 5,225,199 A | 7/1993 | Hidaka et al. |
| 5,240,711 A | 8/1993 | Hille et al. |
| 5,336,210 A | 8/1994 | Hidaka et al. |
| 5,486,362 A | 1/1996 | Kitchell et al. |
| 5,552,406 A | 9/1996 | Mendelson et al. |
| 5,613,958 A | 3/1997 | Kochinke et al. |
| 5,882,676 A * | 3/1999 | Lee ..................... A61K 9/0014 424/448 |
| 6,004,969 A | 12/1999 | Hu |
| 6,090,405 A | 7/2000 | Ninomiya et al. |
| 6,344,211 B1 | 2/2002 | Hille |
| 7,056,527 B2 | 6/2006 | Maruo et al. |
| RE41,408 E | 6/2010 | Reder et al. |
| 2002/0182247 A1* | 12/2002 | Maruo et al. .................. 424/449 |
| 2003/0139698 A1* | 7/2003 | Hyson .............................. 602/61 |
| 2004/0102468 A1* | 5/2004 | Bartholomaeus et al. ... 514/282 |
| 2004/0102476 A1* | 5/2004 | Chan et al. .................... 514/317 |
| 2005/0196418 A1 | 9/2005 | Yu et al. |
| 2007/0298091 A1 | 12/2007 | Kugelmann et al. |
| 2009/0130127 A1* | 5/2009 | Tokumoto ................. C12N 7/00 424/184.1 |
| 2010/0119585 A1 | 5/2010 | Hille et al. |
| 2011/0104241 A1* | 5/2011 | Ohtake ................ A61K 9/0014 424/443 |
| 2012/0201891 A1 | 8/2012 | Cottrell et al. |

FOREIGN PATENT DOCUMENTS

| | | |
|---|---|---|
| CN | 101861148 A | 10/2010 |
| EP | 0368409 | 5/1990 |
| EP | 0375689 | 7/1990 |
| EP | 0432945 | 6/1991 |
| EP | 1174137 A1 | 1/2002 |
| JP | H0630983 A | 2/1994 |
| JP | H07-10754 A | 1/1995 |
| JP | H08512054 A | 12/1996 |
| JP | 2000-511936 A | 9/2000 |
| JP | 2006248996 A | 9/2006 |
| JP | 2008255038 A | 10/2008 |
| WO | 9619975 | 7/1996 |

(Continued)

OTHER PUBLICATIONS

English Translation of WO2012163665. Translated from EPO on Sep. 7, 2016.*
Barrett et al., "The pharmacokinetics and physiological effects of buprenorphine infusion in premature neonates", Br J Clin Pharmacol, 36(3):215-219, (1993).
Barry et al., "Modern Methods of Promoting Drug Absorption Through the Skin", Mol Aspects Med, 12(3):195-241, (1991).
Berner, "Pharmacokinetics of Transdermal Drug Delivery", Journal of Pharmaceutical Sciences, 74(7):718-721, (1985).
Berner et al., "Pharmacokinetic Characterisation of Transdermal Delivery Systems", Clin Pharmacokinet, 26(2):121-134, (1994).

(Continued)

*Primary Examiner* — Doan T Phan
(74) *Attorney, Agent, or Firm* — Bret E. Field; Bozicevic, Field & Francis LLP

(57) ABSTRACT

Aspects of the invention include extended transdermal delivery devices for delivering buprenorphine to a subject for an extended period of time, where the transdermal delivery devices include buprenorphine, an α-hydroxy acid and a pressure sensitive adhesive. In certain instances, buprenorphine, α-hydroxy acid and the pressure sensitive adhesive are provided as a single matrix layer formulation. Also provided are methods of using the subject extended transdermal delivery devices, as well as kits containing the extended transdermal delivery device.

13 Claims, 11 Drawing Sheets

(56) References Cited

FOREIGN PATENT DOCUMENTS

| WO | WO9836728 A2 | 8/1998 | |
|---|---|---|---|
| WO | WO00/35456 A1 | 6/2000 | |
| WO | WO-0045797 A1 * | 8/2000 | ............. A61K 9/006 |
| WO | WO03035456 A1 | 5/2003 | |
| WO | WO2007077741 A1 | 7/2007 | |
| WO | WO2012065740 A1 | 5/2012 | |
| WO | WO2012163665 A1 | 12/2012 | |

OTHER PUBLICATIONS

Bohme, "Buprenorphine in a Transdermal Therapeutic System—A New Option", Clin Rhematol, (Suppl 1):S13-S16 , (2002).

Cassidy et al., "Controlled buccal delivery of buprenorphine", Journal of Controlled Release, 25(1-2):21-29, (1993).

Cleary, "2. Pharmacokinetic Interpretation", Topical Drug Bioavailability, Bioequivalence, and Penetration, Chapter 2, p. 17-52, Published by Springer Press in New York in 1993.

Grond et al., "Clinial Pharmacokinetics of Transdermal Opioids", Clin Pharmacokinet, 38(1):59-89, (2000).

Donner et al., "Direct conversion from oral morphine to transdermal fentanyl: a multicenter study in patients with cancer pain", Pain, 64(3):527-534, (1996).

Gupta et al., "System Functionality and Physicochemical Model of Fentanyl Transdermal System", J. Pain, and Symptom. Manage, 7(3 Suppl):S17-S26, (1992).

Guy et al., "Rate control in transdermal drug delivery?", International Journal of Pharmaceutics, 82(3):R1-R6, (1992).

Lehmann et al., "Transdermal Fentanyl: Clinical Pharmacology", J Pain Symptom Manage, 7(3 Suppl):S8-S16, (1992).

Levy et al., "Transdermal Fentanyl: Seeding Trial in Patients with Chronic Cancer Pain", J Pain and Symptom Manage, 7(3 Suppl):S48-S50, (1992).

Ling et al., "A Controlled Trial Comparing Buprenorphine and Methadone Maintenance in Opioid Dependence", Arch Gen Psychiatry 53(5):401-407, (1996).

Marquardt et al., "Fentenyl Remaining in a Transdermal System Following Three Days of Continuous Use", Ann Pharmacother, 29(10):696-71, (1995).

McQuinn et al., "Sustained oral mucosal delivery in human volunteers of buprenorphine from a thin non-eroding mucoadhesive polymetric disk", Journal of Controlled Release, 34(3):243-250, (1995).

Miskolczi et al., "Human pharmacokinetics of analgesics and methods for their determination in biological fluids", J Pharm Biomed Anal, 3(3):209-226, (1985).

Nightingale et al., "Flow-Through System Effects on in Vitro Analysis of Transdermal Systems", Pharmaceutical Research, 10(10):1521-1526, (1993).

Roy et al., "Solubility and Related Physicochemical Properties of Narcotic Analgesics", Pharmaceutical Research, 5(9):580-586, (1988).

Roy et al., "Transdermal Delivery of Buprenorphine through Cadaver Skin", J Pharm Sci., 83(2):126-30, (1994).

Russo et al., "A Clinical snapshot of transdermal buprenorphine in pain management", European Journal of Pain Supplements, 1(1):74-77, (2007).

Schmid-Grendelmeier et al., "A comparison of the skin irritation potential of transdermal fentanyl versus transdermal buprenorphine in middle-aged to elderly healthy volunteers", Current Medical Research and Opinion, 22(3):501-509, (2006).

Simmonds et al., "Transdermal Fentanyl: Long-Term Analgesic Studies", Journal of Pain and Symptom Management, 7(3 Suppl):S36-S39, (1992).

Stinchcomb et al., "Permeation of Buprenorphine and Its 3-Alkyl-Ester Prodrugs Through Human Skin", Pharmaceutical Research, 13(10):1519-1523, (1996).

Wilding et al., "Pharmacokinetic evaluation of transdermal buprenorphine in man", International Journal of Pharmaceutics, 132(1-2):81-87, (1996).

Eltahtawy et al., "7-Day Bioavailability of Buprenorphine from a Novel Transdermal System in Demographic Subgroups", Abstract 56 from the Abstracts Thirtieth Annual Meeting American College of Clinical Pharmacology Sep. 23-25, 2001, J. Clin. Pharmacol. 41:1027, (2001).

Reidenberg et al., "Daily Pharmacokinetic Performance of a Buprenorphine Transdermal System (BTDS) for up to 7 Days". Abstract 57 from the Abstracts Thirtieth Annual Meeting American College of Clinical Pharmacology Sep. 23-25, 2001, J. Clin. Pharmacol. 41:1027, (2001).

* cited by examiner

EXTENDED BUPRENORPHINE TRANSDERMAL DELIVERY COMPOSITIONS AND METHODS FOR USING THE SAME

CROSS-REFERENCE TO RELATED APPLICATIONS

Pursuant to 35 U.S.C. § 119(e), this application claims priority to the filing date of U.S. Provisional Application Ser. No. 61/746,832 filed Dec. 28, 2012, the disclosure of which is herein incorporated by reference.

INTRODUCTION

Prolonged analgesia is desirable in patients suffering from moderate to severe pain. Buprenorphine is a synthetic opiate agonist analgesic derived from oripavine and thebaine and is used clinically as a potent analgesic for the relief of acute and chronic pain because of its extremely high binding affinity at the γ- and κ-opioid receptors. It has partial agonist activity at the μ-opioid receptor, partial or full agonist activity at the ORL1/nociception and δ-opioid receptors, and competitive antagonist activity at the κ-opioid receptor.

Available oral analgesics provide a duration of pain-relief effect for a time period which requires that the drug be administered to a patient multiple (i.e., 2 or more) times per day. During treatment, there may be a need to administer a sustained amount of analgesics into the human body. Oral administration is a commonly used method because of its simplicity. However, oral administration is often complicated with gastrointestinal irritation and drug metabolism in the liver. Administration through human skin (i.e., transdermal drug delivery) is an alternative route and can provide advantages over oral administration including avoidance of first pass metabolism, controlled delivery, simple dosing regimens, and improved patient compliance. Transdermal delivery systems are patches that contain an active agent that are adhered to the skin to deliver the active agents by percutaneous absorption. After a transdermal patch is applied to the skin, the active agent contained in the patch passes through, or permeates the skin and can reach its site of action through a systemic blood flow. Alternatively, a transdermal patch may be placed on the desired treatment site such that the medication contained in the patch is delivered locally.

SUMMARY

Aspects of the invention include extended transdermal delivery devices for delivering buprenorphine to a subject for an extended period of time, where the transdermal delivery devices include buprenorphine, an α-hydroxy acid and a pressure sensitive adhesive. In certain instances, buprenorphine, α-hydroxy acid and the pressure sensitive adhesive are provided as a single matrix layer formulation. Also provided are methods of using the subject extended transdermal delivery devices, as well as kits containing the extended transdermal delivery devices.

In some embodiments, an extended transdermal delivery device which includes a buprenorphine composition having an amount of buprenorphine, an α-hydroxy acid and a pressure sensitive adhesive in a single matrix layer formulated to deliver buprenorphine to a subject for seven days or longer is provided. In some instances, buprenorphine compositions include buprenorphine free base. In other embodiments, an extended transdermal delivery device which includes a buprenorphine composition having an amount of buprenorphine, an α-hydroxy acid where the molar ratio of α-hydroxy acid to buprenorphine is 2 or greater is provided. For example, the extended transdermal delivery device may include a buprenorphine composition having an amount of buprenorphine and α-hydroxy acid such where the molar ratio of α-hydroxy acid to buprenorphine is 5 or greater. In yet other embodiments, an extended transdermal delivery device which includes a buprenorphine composition having an amount of buprenorphine and an α-hydroxy acid where the weight ratio of α-hydroxy acid is 50% or less than the weight ratio of buprenorphine is provided.

In certain embodiments, the subject extended transdermal delivery devices having an amount of buprenorphine, an α-hydroxy acid and a pressure sensitive adhesive may be configured to deliver 75% or greater of the buprenorphine in the buprenorphine composition. For example, the extended transdermal delivery device may be configured to deliver 90% or greater of buprenorphine in the buprenorphine composition over the course of 7 days or longer.

In other embodiments, the subject extended transdermal delivery devices having an amount of buprenorphine, an α-hydroxy acid and a pressure sensitive adhesive may be configured to provide a transdermal buprenorphine flux for an extended period of time which is within 90% or greater of peak transdermal buprenorphine flux when measured by an in-vitro protocol, such as for example protocols employing human cadaver skin with epidermal layers (stratum corneum and epidermis) in a Franz cell having donor and receptor sides clamped together and receptor solution containing phosphate buffer. For example, in these instances, the transdermal delivery device may be configured to provide a peak transdermal buprenorphine flux of 1.5 μg/cm$^2$/hr or greater, such as 2.0 μg/cm$^2$/hr or greater.

In other embodiments, extended transdermal delivery devices of interest having an amount of buprenorphine, an α-hydroxy acid and a pressure sensitive adhesive may be configured to deliver an average cumulative amount of buprenorphine of 60 μg/cm$^2$ or greater over an extended period of time. For example, the extended transdermal delivery device may be configured to deliver an average cumulative amount of buprenorphine of 75 μg/cm$^2$ or greater. In certain instances, the subject extended transdermal delivery devices may be configured to deliver buprenorphine in an amount that is substantially linear over the course of the 7 days or longer.

DETAILED DESCRIPTION

Figure 1:
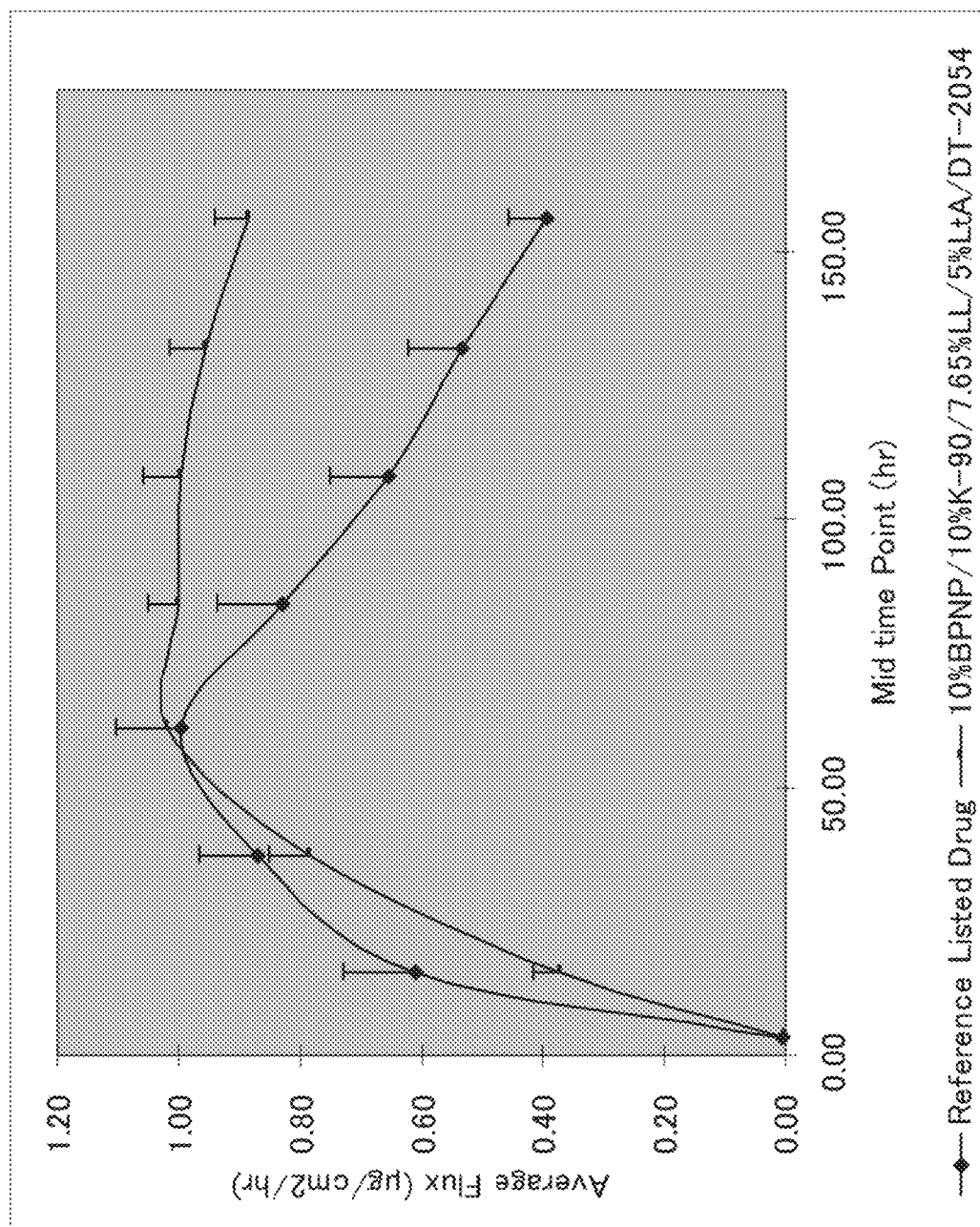
FIG. 1 shows an example of data acquired for determining average buprenorphine flux as a function of extended transdermal delivery device application time according to one embodiment.

Aspects of the invention include extended transdermal delivery devices for delivering buprenorphine to a subject for an extended period of time, where the transdermal delivery devices includes buprenorphine, an α-hydroxy acid and a pressure sensitive adhesive. In certain instances, buprenorphine, α-hydroxy acid and the pressure sensitive adhesive are provided as a single matrix layer formulation. Also provided are methods of using the subject extended transdermal delivery devices, as well as kits containing the extended transdermal delivery device.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing various embodiments of the invention, aspects of the extended transdermal delivery devices having buprenorphine and an α-hydroxy acid are reviewed first in greater detail, followed by a detailed description of embodiments of using the transdermal delivery systems and a review of kits that include the subject extended transdermal delivery devices.

Extended Buprenorphine Transdermal Delivery Devices Containing Buprenorphine Compositions As described in detail above, aspects of the invention include extended buprenorphine transdermal delivery devices for delivering buprenorphine to a subject for an extended period of time. The transdermal delivery devices include buprenorphine, an α-hydroxy acid and a pressure sensitive adhesive. The term "transdermal" is used in its conventional sense to refer to the route of administration where an active agent (i.e., drug) is delivered across the skin (e.g., topical administration) or mucous membrane for systemic distribution. As such, transdermal buprenorphine compositions as described herein include compositions which are delivered to the subject through one or more of the subcutis, dermis and epidermis, including the stratum corneum, stratum germinativum, stratum spinosum and stratum basale. Accordingly, extended transdermal delivery devices containing a transdermal buprenorphine composition can be configured to be applied at any convenient location, such as for example, the arms, legs, buttocks, abdomen, back, neck, scrotum, vagina, face, behind the ear, buccally as well as sublingually. In describing methods of the present invention, the term "subject" is meant the person or organism to which the transdermal composition is applied and maintained in contact. As such, subjects of the invention may include but are not limited to mammals, e.g., humans and other primates, such as chimpanzees and other apes and monkey species; and the like, where in certain embodiments the subject are humans.

The term "extended transdermal delivery" is used herein to refer to a buprenorphine composition formulated to be delivered over an extended period of time, such as over the course of hours, days and including weeks. In some embodiments, extended transdermal delivery devices are configured for multi-day delivery of a therapeutically effective amount of the buprenorphine active agent that is topically applied to the skin of a subject. By multi-day delivery is meant that the transdermal composition is formulated to provide a therapeutically effective amount for a period of time that is 1 day or longer, such as 2 days or longer, such as 3 days or longer, such as 5 days or longer, such as 7 days or longer, including 10 days or longer. In certain embodiments, extended transdermal delivery devices provided by the present invention are configured to provide a therapeutically effective amount of buprenorphine to a subject for a period of 7 days or longer.

Buprenorphine is described by the formula:

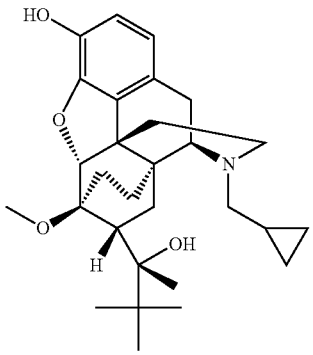

Buprenorphine may be applied to the subject as a free base or salt, such as for example as a pharmaceutically acceptable salt including, but not limited to, a mesylate, maleate, fumarate, tartrate, hydrochloride, hydrobromide, esylate, p-toluenesulfonate, benzoate, acetate, phosphate and sulfate salt. For example, in certain instances, applying a transdermal buprenorphine composition to a subject includes applying buprenorphine as a free base. In other instances, applying a transdermal buprenorphine composition to a subject includes applying buprenorphine as a pharmaceutically acceptable salt. Buprenorphine in transdermal buprenorphine compositions may be a racemic mixture or as a pure enantiomer, such as the R or L enantiomer of the active agent.

Depending on the site of application and physiology of the subject and exposed surface area of the extended transdermal delivery device, the amount of buprenorphine in compositions of interest may vary, in some instances, the amount of buprenorphine ranging from 0.01 mg to 50 mg, such as 0.05 mg to 40 mg, such as 0.1 to 30 mg, such as 1 to 20 mg, and including 1 mg to 10 mg. In some embodiments, the amount of buprenorphine in the transdermal composition ranges from 1% to 15% w/w, such as 2% to 15% w/w, such as 3% to 12.5%, such as 4% to 11% w/w and including 5% to 10% w/w. In other embodiments, the amount of buprenorphine in the subject transdermal compositions is 10% by weight or less of the total weight of the transdermal composition, such as 9% by weight or less, such as 8% by weight or less, such as 7% by weight or less, such as 6% by weight or less, such as 5% by weight or less and including 3% by weight or less of the total weight of the transdermal composition.

As reviewed above, the transdermal buprenorphine composition also includes an α-hydroxy acid. The term "α-hydroxy acid" is used in its conventional sense to refer to the class of chemical compounds having a carboxylic acid substituted with a hydroxyl group on an adjacent carbon, such as for example, a compound defined by the formula:

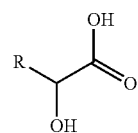

where R is hydrogen, alkyl, substituted alkyl, cycloalkyl, substituted cycloalkyl, aryl or substituted aryl. In certain embodiments, R is hydrogen. In other embodiments, R is a C1-C12 alkyl, such as methyl or a carboxylic acid substituted alkyl. In yet other embodiments, R is aryl. In certain embodiments, α-hydroxy acids of interest include glycolic acid, lactic acid, tartaric acid, citric acid, malic acid and mandelic acid and combinations thereof, among others.

Depending on the site of application and physiology of the subject and exposed surface area of the extended transdermal delivery device, the amount of α-hydroxy acid in transdermal compositions of interest may vary, the amount of α-hydroxy acid ranging from 0.1 mg to 500 mg, such as 0.5 mg to 400 mg, such as 1 to 300 mg, such as 10 to 200 mg, and including 10 mg to 100 mg. As such, the amount of α-hydroxy acid in the transdermal composition ranges from 2% to 30% w/w, such as 4% to 30% w/w, such as 5% to 25%, such as 6% to 22.5% w/w and including 10% to 20% w/w. In other embodiments, the amount of α-hydroxy acid in the subject transdermal compositions is 2% by weight or greater of the total weight of the transdermal composition, such as 4% by weight or greater, such as 6% by weight or greater, such as 8% by weight or greater, such as 10% by weight or greater, such as 12% by weight or greater and including 15% by weight or greater of the total weight of the transdermal composition.

The weight ratio of α-hydroxy acid to buprenorphine in the subject compositions may range from 1:2 and 1:2.5; 1:2.5 and 1:3; 1:3 and 1:3.5 1:3.5 and 1:4; 1:4 and 1:4.5; 1:4.5 and 1:5; 1:5 and 1:10; and 1:10 and 1:25 or a range thereof. For example, the weight ratio of α-hydroxy acid to buprenorphine in compositions of interest may range between 1:1 and 1:5; 1:5 and 1:10; 1:10 and 1:15; or 1:15 and 1:25. Alternatively, the weight ratio of buprenorphine to α-hydroxy acid in the subject compositions ranges between 2:1 and 2.5:1; 2.5:1 and 3:1; 3:1 and 3.5:1; 3.5:1 and 4:1; 4:1 and 4.5:1; 4.5:1 and 5:1; 5:1 and 10:1; and 10:1 and 25:1 or a range thereof. For example, the ratio of buprenorphine to α-hydroxy acid in compositions of interest may range between 1:1 and 5:1; 5:1 and 10:1; 10:1 and 15:1; or 15:1 and 25:1.

In certain embodiments, extended transdermal delivery devices of the invention include a buprenorphine composition having buprenorphine and an α-hydroxy acid where the molar ratio of α-hydroxy acid to buprenorphine is 2 or greater, such as a molar ratio of 3 or greater, such as a molar ratio of 4 or greater and including a molar ratio of 10 or greater. In certain instances, the extended transdermal delivery device may include a buprenorphine composition having an amount of buprenorphine and α-hydroxy acid such where the molar ratio of α-hydroxy acid to buprenorphine is 5 or greater.

In other embodiments, the extended transdermal delivery device contains a transdermal buprenorphine composition having an amount of buprenorphine and α-hydroxy acid where the weight ratio of α-hydroxy acid is 50% or less than the weight ratio of buprenorphine, such as 40% or less, such as 30% or less and including a weight ratio of α-hydroxy acid that is 25% or less than the weight ratio of buprenorphine. For example, in these embodiments, where the buprenorphine is 10% by weight of the total weight of the transdermal buprenorphine composition, α-hydroxy acid is 5% by weight or less of the total weight of the transdermal buprenorphine composition, such as 4% by weight or less, such as 3% by weight or less and including 2% by weight or less of the total weight of the transdermal buprenorphine composition. In another instance, where the buprenorphine is 7% by weight of the total weight of the transdermal buprenorphine composition, α-hydroxy acid is 3.5% by weight or less of the total weight of the transdermal buprenorphine composition, such as 3% by weight or less, such as 2.5% by weight or less and including 1.5% by weight or less of the total weight of the transdermal buprenorphine composition. In another instance, where the buprenorphine is 4% by weight of the total weight of the transdermal buprenorphine composition, α-hydroxy acid is 2% by weight or less of the total weight of the transdermal buprenorphine composition, such as 1.9% by weight or less, such as 1.8% by weight or less and including 1.5% by weight or less of the total weight of the transdermal buprenorphine composition. In yet another instance, where buprenorphine is 15% by weight of the total weight of the transdermal buprenorphine composition, α-hydroxy acid is 7.5% by weight or less of the total weight of the transdermal buprenorphine composition, such as 7% by weight or less, such as 5% by weight or less and including 3% by weight or less of the total weight of the transdermal buprenorphine composition.

In embodiments of the present invention, transdermal buprenorphine compositions may also include a pressure sensitive adhesive. Pressure sensitive adhesives may include but are not limited to poly-isobutene adhesives, polyisobutylene adhesives, poly-isobutene/polyisobutylene adhesive mixtures, carboxylated polymers, acrylic or acrylate copolymers, such as carboxylated acrylate copolymers. Acrylate copolymers of interest include copolymers of various monomers, such as "soft" monomers, "hard" monomers or "functional" monomers. The acrylate copolymers can be composed of a copolymer including bipolymer (i.e., made with two monomers), a terpolymer (i.e., made with three monomers), or a tetrapolymer (i.e., made with four monomers), or copolymers having greater numbers of monomers. The acrylate copolymers may be crosslinked or non-crosslinked. The polymers can be cross-linked by known methods to provide the desired polymers. The monomers from of the acrylate copolymers may include at least two or more exemplary components selected from the group including acrylic acids, alkyl acrylates, methacrylates, copolymerizable secondary monomers or monomers with functional groups. Monomers ("soft" and "hard" monomers) may be methoxyethyl acrylate, ethyl acrylate, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, tridecyl methacrylate, acrylonitrile, methoxyethyl acrylate, methoxyethyl methacrylate, and the like. Additional examples of acrylic adhesive monomers are described in Satas, "Acrylic Adhesives," Handbook of Pressure-Sensitive Adhesive Technology, 2nd ed., pp. 396-456 (D. Satas, ed.), Van Nostrand Reinhold, New York (1989), the disclosure of which is herein incorporated by reference. In some embodiments, the pressure sensitive adhesive is an acrylate-vinyl acetate copolymer. In some embodiments, the pressure sensitive adhesive may be a composition that is, or is substantially the same as, the composition of DuroTak® 87-200A, DuroTak®87-2353, DuroTak®87-2100, DuroTak®87-2051, DuroTak®87-2052, DuroTak®87-2194, DuroTak®87-2677, DuroTak®87-201A, DuroTak®87-2979, and DuroTak®87-2074 and combinations thereof. The term "substantially the same" as used herein refers to a composition that is an acrylate-vinyl acetate copolymer in an organic solvent solution. In certain embodiments, the acrylic pressure-sensitive adhesive is DuroTak®87-2054.

Depending on the site of application and physiology of the subject and exposed surface area of the extended transdermal delivery device, the amount of pressure sensitive adhesive in transdermal buprenorphine compositions of interest may vary, the amount of pressure sensitive adhesive ranging from 0.1 mg to 500 mg, such as 0.5 mg to 400 mg, such as 1 to 300 mg, such as 10 to 200 mg, and including 10 mg to 100 mg. As such, the amount of pressure sensitive adhesive in the transdermal composition ranges from 2% to 30% w/w, such as 4% to 30% w/w, such as 5% to 25%, such as 6% to 22.5% w/w and including 10% to 20% w/w. In other embodiments, the amount of pressure sensitive adhesive in the subject transdermal compositions is 8% by weight or greater of the total weight of the transdermal composition, such as 10% by weight or greater, such as 12% by weight or greater, such as 15% by weight or greater, such as 20% by weight or greater, such as 25% by weight or greater and including 30% by weight or greater of the total weight of the transdermal composition.

Transdermal buprenorphine compositions of interest may also include one or more esters of the α-hydroxy acid. For example, where the α-hydroxy acid present in the transdermal buprenorphine composition is lactic acid, subject transdermal buprenorphine compositions may also include lactate. Likewise, where the α-hydroxy acid present in the transdermal buprenorphine composition is malic acid, subject transdermal buprenorphine composition may also include malate. In yet other instances, where the α-hydroxy acid present in the transdermal buprenorphine composition is citric acid, subject transdermal buprenorphine compositions may also include citrate.

Depending on the site of application and physiology of the subject and exposed surface area of the extended transdermal delivery device, the amount of α-hydroxy acid ester in transdermal buprenorphine compositions of interest may vary, the amount of α-hydroxy acid ester ranging from 0.1 mg to 500 mg, such as 0.5 mg to 400 mg, such as 1 to 300 mg, such as 10 to 200 mg, and including 10 mg to 100 mg. As such, the amount of α-hydroxy acid ester in the transdermal composition ranges from 2% to 30% w/w, such as 4% to 30% w/w, such as 5% to 25%, such as 6% to 22.5% w/w and including 10% to 20% w/w. In other embodiments, the amount of α-hydroxy acid ester in the subject transdermal compositions is 2% by weight or greater of the total weight of the transdermal composition, such as 4% by weight or greater, such as 6% by weight or greater, such as 8% by weight or greater, such as 10% by weight or greater, such as 12% by weight or greater and including 15% by weight or greater of the total weight of the transdermal composition.

In some embodiments, transdermal buprenorphine compositions may further include one or more crosslinked hydrophilic polymers. For example, the crosslinked hydrophilic polymer may be a methacrylic acid copolymer. By "methacrylic acid copolymer" is meant the class of polymeric compounds described by the formula:

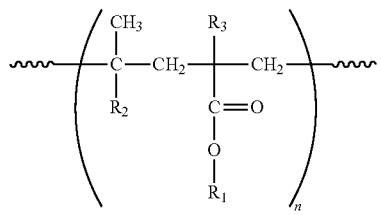

wherein $R_1$ is —H or a C1-C12 alkyl; $R_2$ is an anionic moiety, such as a carboxylic acid (i.e., —COOH) and $R_3$ is —H or a C1-C12 alkyl. The size of the methacrylic acid copolymer may vary, where n may be 50 or greater, such as 75 or greater, such as 100 or greater, such as 200 or greater, such as 350 or greater, such as 500 or greater and including 750 or greater. As such, the molecular weight of the subject methacrylic acid copolymer may be 5 kDa or greater, such as 10 kDa or greater, such as 25 kDa or greater, such as 50 kDa or greater, such as 60 kDa or greater, such as 70 kDa or greater, such as 100 kDa or greater, such as 135 kDA or greater and including 150 kDa or greater.

In certain embodiments, $R_1$ and $R_3$ is alkyl and $R_2$ is an anionic moiety, such as a carboxylic acid. In these embodiments, $R_1$ and $R_3$ may be methyl, ethyl, propyl, butyl, pentyl, isobutyl, isopropyl, tert-butyl, among other straight chain or branched alkyls and $R_2$ may be a carboxylic acid. For example, in certain instances, $R_1$ is ethyl, $R_2$ is carboxylic acid and $R_3$ is methyl.

In some embodiments, the methacrylic acid copolymer is substantially the same as a Eudragit® methacrylic acid copolymer. The term "Eudragit® methacrylic acid copolymer" is used in its conventional sense to refer to copolymers derived from esters of acrylic and methacrylic acid. In embodiments of the invention, Eudragit® polymers may be methacrylic acid copolymers (e.g., functional group being carboxylic acid). In certain embodiments, the Eudragit® polymer is a methacrylic acid Eudragit® polymer, such as Eudragit® L100 or Eudragit® L100-55.

In other embodiments, the crosslinked polymer is an amine-containing hydrophilic polymer. Amine-containing polymers may include, but are not limited to, polyethyleneimine, amine-terminated polyethylene oxide, amine-terminated polyethylene/polypropylene oxide, polymers of dimethyl amino ethyl methacrylate, and copolymers of dimethyl amino ethyl methacrylate and vinyl pyrrolidone. In certain embodiments, the crosslinked polymer is polyvinylpyrrolidone, such as for example PVP K90.

The amount of crosslinked polymer in transdermal compositions of interest may vary, the amount of crosslinked polymer ranging from 0.1 mg to 500 mg, such as 0.5 mg to 400 mg, such as 1 to 300 mg, such as 10 to 200 mg, and including 10 mg to 100 mg. As such, the amount of crosslinked polymer in the transdermal composition ranges from 2% to 30% w/w, such as 4% to 30% w/w, such as 5% to 25%, such as 6% to 22.5% w/w and including 10% to 20% w/w. In other embodiments, the amount of crosslinked polymer in the subject transdermal compositions is 8% by weight or greater of the total weight of the transdermal composition, such as 10% by weight or greater, such as 12% by weight or greater, such as 15% by weight or greater, such as 20% by weight or greater, such as 25% by weight or greater and including 30% by weight crosslinked polymer or greater of the total weight of the transdermal composition.

In certain embodiments, the subject transdermal buprenorphine compositions further include a percutaneous absorption enhancer. The percutaneous absorption enhancer may facilitate the permeation of the buprenorphine through the skin or mucous membrane of the subject, such as for example to reduce the amount of buprenorphine required. The percutaneous absorption enhancer may be applied and maintained in conjunction with the transdermal composition of buprenorphine in an amount ranging from 2% to 25% (w/w), such as from 5% to 20% (w/w), and including from 5% to 15% (w/w). Example percutaneous absorption enhancers may include, but is not limited to aliphatic alcohols, such as saturated or unsaturated higher alcohols having 12 to 22 carbon atoms (e.g., oleyl alcohol or lauryl alcohol); fatty acids, such as linolic acid, oleic acid, linolenic acid, stearic acid, isostearic acid and palmitic acid; fatty acid esters, such as isopropyl myristate, diisopropyl adipate, and isopropyl palmitate; alcohol amines, such as triethanolamine, triethanolamine hydrochloride, and diisopropanolamine; polyhydric alcohol alkyl ethers, such as alkyl ethers of polyhydric alcohols such as glycerol, ethylene glycol, propylene glycol, 1,3-butylene glycol, diglycerol, polyglycerol, diethylene glycol, polyethylene glycol, dipropylene glycol, polypropylene glycol, sorbitan, sorbitol, isosorbide, methyl glucoside, oligosaccharides, and reducing oligosaccharides, where the number of carbon atoms of the alkyl group moiety in the polyhydric alcohol alkyl ethers is preferably 6 to 20; polyoxyethylene alkyl ethers, such as polyoxyethylene alkyl ethers in which the number of carbon atoms of the alkyl group moiety is 6 to 20, and the number of repeating units (e.g. —O—CH$_2$CH$_2$—) of the polyoxyethylene chain is 1 to 9, such as but not limited to polyoxyethylene lauryl ether, polyoxyethylene cetyl ether, polyoxyethylene stearyl ether, and polyoxyethylene oleyl ether; glycerides (i.e., fatty acid esters of glycerol), such as glycerol esters of fatty acids having 6 to 18 carbon atoms, where the glycerides may be monoglycerides (i.e., a glycerol molecule covalently bonded to one fatty acid chain through an ester linkage), diglycerides (i.e., a glycerol molecule covalently bonded to two fatty acid chains through ester linkages), triglycerides (i.e., a glycerol molecule covalently bonded to three fatty acid chains through ester linkages), or combinations thereof, where the fatty acid components forming the glycerides include octanoic acid, decanoic acid, dodecanoic acid, tetradecanoic acid, hexadecanoic acid, octadecanoic acid (i.e., stearic acid) and oleic acid; middle-chain fatty acid esters of polyhydric alcohols; lactic acid alkyl esters; dibasic acid alkyl esters; acylated amino acids; pyrrolidone; pyrrolidone derivatives and combinations thereof. Additional types of percutaneous absorption enhancers may include lactic acid, tartaric acid, 1,2,6- hexanetriol, benzyl alcohol, lanoline, potassium hydroxide (KOH), tris(hydroxymethyl)aminomethane, glycerol monooleate (GMO), sorbitan monolaurate (SML), sorbitan monooleate (SMO), laureth-4 (LTH), and combinations thereof.

In certain embodiments, transdermal buprenorphine compositions further include a fatty acid ester. By "fatty acid ester" is meant the class of chemical ester compounds that result from the combination of a fatty acid with an alcohol. In certain embodiments, fatty acid esters of interest include glycerides (i.e., fatty acid esters of glycerol), such as glycerol esters of fatty acids having 6 to 18 carbon atoms, where the glycerides may be monoglycerides (i.e., a glycerol molecule covalently bonded to one fatty acid chain through an ester linkage), diglycerides (i.e., a glycerol molecule covalently bonded to two fatty acid chains through ester linkages), triglycerides (i.e., a glycerol molecule covalently bonded to three fatty acid chains through ester linkages), or combinations thereof, where the fatty acid components forming the glycerides include octanoic acid, decanoic acid, dodecanoic acid, tetradecanoic acid, hexadecanoic acid, octadecanoic acid (i.e., stearic acid) and oleic acid; middle-chain fatty acid esters of polyhydric alcohols; lactic acid alkyl esters; dibasic acid alkyl esters; acylated amino acids; pyrrolidone; pyrrolidone derivatives and combinations thereof. For example, fatty acid esters of interest may include lauryl lactate, oleyl oleate or glycerol monoleate and combinations thereof, among other fatty acid esters.

The amount of fatty acid ester in transdermal compositions of interest may vary, the amount of fatty acid ester ranging from 0.1 mg to 1000 mg, such as 0.5 mg to 750 mg, such as 1 to 500 mg, such as 10 to 400 mg, and including 10 mg to 300 mg. As such, the amount of fatty acid ester in the transdermal composition ranges from 2% to 50% w/w, such as 4% to 45% w/w, such as 5% to 40%, such as 6% to 35% w/w and including 10% to 30% w/w. In other embodiments, the amount of fatty acid ester is 10% by weight or greater of the total weight of the transdermal composition, such as 10% by weight or greater, such as 12% by weight or greater, such as 15% by weight or greater, such as 20% by weight or greater, such as 25% by weight or greater and including 30% by weight or greater of the total weight of the transdermal composition.

In certain embodiments, transdermal buprenorphine compositions of interest further include water. The amount of water in transdermal compositions of interest may vary, the amount of water ranging from 0.1 mg to 500 mg, such as 0.5 mg to 400 mg, such as 1 to 300 mg, such as 10 to 200 mg, and including 10 mg to 100 mg. As such, the amount of water in the transdermal composition ranges from 0.01% to 2% w/w, such as 0.025% to 1.5% w/w, such as 0.05% to 1.25% w/w, such as 0.1% to 1.1% w/w, such as 0.2% to 1.0% w/w and including 0.24% to 0.9% w/w. In other embodiments, the amount of water is 0.01% by weight or greater of the total weight of the transdermal composition, such as 0.025% by weight or greater, such as 0.05% by weight or greater, such as 0.1% by weight or greater, such as 0.25% by weight or greater and including 0.9% by weight water or greater of the total weight of the transdermal composition.

As such, the formulation of the subject transdermal buprenorphine composition may vary. For example, compositions of the invention may be in the form of a liquid solution or suspension, syrup, gel, foam or any combination thereof for application by the extended transdermal delivery device.

In some embodiments, the extended transdermal delivery device is configured as a single layer. By "single layer" is meant that the extended transdermal delivery device includes only a single layer of buprenorphine composition disposed on the surface of a substrate of the extended transdermal delivery device and does not include separate distinct layers for the pressure sensitive adhesive, transdermal buprenorphine composition, or if present any permeation enhancers. Likewise, single layer extended transdermal delivery devices of the present invention do not further include a separate buprenorphine reservoir (i.e., active agent reservoir) separate from the pressure sensitive adhesive. As such, single layer extended transdermal delivery devices of the present invention may include in a single matrix an amount of each of the components of the transdermal buprenorphine compositions. For example, in some embodiments, single layer extended transdermal delivery devices of interest include a single layer matrix of an amount of buprenorphine, an α-hydroxy acid and a pressure sensitive adhesive. In another embodiment, single layer extended transdermal delivery devices of interest include a single layer matrix of an amount of buprenorphine, an α-hydroxy acid, a pressure sensitive adhesive and an α-hydroxy acid ester. In another embodiment, single layer extended transdermal delivery devices of interest include a single layer matrix of an amount of buprenorphine, an α-hydroxy acid, a pressure sensitive adhesive, an α-hydroxy acid ester and a fatty acid ester. In yet another embodiment, single layer extended transdermal delivery devices of interest include a single layer matrix of an amount of buprenorphine, an α-hydroxy acid, a pressure sensitive adhesive, an α-hydroxy acid ester, a fatty acid ester and water. Depending on the length of the dosage interval and the desired target dosage, the thickness of single layer matrices of interest may vary, in some instances ranging in thickness from 10-200 micron, such as from 20-175 micron, such as 25-150 micron, such as 35-140 micron, such as 40-125 micron mm and including 50-100 micron The size of subject extended transdermal delivery devices may vary, and in some instances the devices are sized to cover the entire application site on the subject. As such, the extended transdermal delivery device may have a length ranging from 2 to 100 cm, such as from 4 to 60 cm and a width ranging from 2 to 100 cm, such as from 4 to 60 cm. As such, the area of the extended transdermal delivery device may range from 4 $cm^2$ to 10,000 $cm^2$, such as from 5 $cm^2$ to 1000 $cm^2$, such as from 10 $cm^2$ to 100 $cm^2$, such as from 15 $cm^2$ to 50 $cm^2$ and including from 20 $cm^2$ to 40 $cm^2$. In certain embodiments, the extended transdermal delivery device is sized to have an area of 25 $cm^2$. In certain instances, the extended transdermal delivery device is insoluble in water. By insoluble in water is meant that that the extended transdermal delivery device may be immersed in water for a period of 1 day or longer, such as 1 week or longer, including 1 month or longer, and exhibit little if any dissolution, e.g., no observable dissolution. In other words, the extended transdermal delivery device is water-resistant and will not change or be altered in any way when in contact with water.

In certain embodiments, the extended transdermal delivery device having an amount of a buprenorphine, an α-hydroxy acid and a pressure sensitive adhesive as described above furthers includes a backing layer. The backing may be flexible, such that it can be brought into close contact with the desired application site on the subject. The backing may be fabricated from a material that it does not absorb the buprenorphine, and does not allow the buprenorphine to be leached from the matrix. Backing layers of interest may include, but is not limited to, non-woven fabrics, woven fabrics, films (including sheets), porous bodies, foamed bodies, paper, composite materials obtained by laminating a film on a non-woven fabric or woven fabric, and combinations thereof.

Non-woven and woven fabric may include polyolefin resins such as polyethylene and polypropylene; polyester resins such as polyethylene terephthalate, polybutylene terephthalate and polyethylene naphthalate; rayon, polyamide, poly(ester ether), polyurethane, polyacrylic resins, polyvinyl alcohol, styrene-isoprene-styrene copolymers, and styrene-ethylene-propylene-styrene copolymers; and combinations thereof. Fabrics may include cotton, rayon, polyacrylic resins, polyester resins, polyvinyl alcohol, and combinations thereof. Films may include polyolefin resins such as polyethylene and polypropylene; polyacrylic resins such as polymethyl methacrylate and polyethyl methacrylate; polyester resins such as polyethylene terephthalate, polybutylene terephthalate and polyethylene naphthalate; and besides cellophane, polyvinyl alcohol, ethylene-vinyl alcohol copolymers, polyvinyl chloride, polystyrene, polyurethane, polyacrylonitrile, fluororesins, styrene-isoprene-styrene copolymers, styrene-butadiene rubber, polybutadiene, ethylene-vinyl acetate copolymers, polyamide, and polysulfone; and combinations thereof. Papers may include impregnated paper, coated paper, wood free paper, Kraft paper, Japanese paper, glassine paper, synthetic paper, and combinations thereof.

Depending on the dosage interval and the desired target dosage, the size of the backing may vary, and in some instances sized to cover the entire application site on the subject. As such, the backing layer may have a length ranging from 2 to 100 cm, such as 4 to 60 cm and a width ranging from 2 to 100 cm, such as 4 to 60 cm. In certain instances, the backing layer may insoluble in water. By insoluble in water is meant that that the backing layer may be immersed in water for a period of 1 day or longer, such as 1 week or longer, including 1 month or longer, and exhibit little if any dissolution, e.g., no observable dissolution. In other words, the backing layer is water-resistant and will not change or be altered in any way when in contact with water.

The subject extended transdermal delivery devices may be configured to deliver buprenorphine by passive or active transport. By "passive transport" is meant that the transdermal delivery device is configured to deliver the buprenorphine composition across the skin or mucous membrane in the absence of applied energy (e.g., rubbing or heat) and is primarily dependent on the permeability of the barrier (e.g., skin or mucous membrane) and by entropy of delivery. Alternatively, the subject transdermal delivery device may be configured to employ active transport, such that the extended transdermal delivery device is configured to transport the composition through the skin or mucous membrane in conjunction with applied energy including, but is not limited to microneedle delivery, facilitated diffusion, electrochemically-produced gradients, iontophoretic systems, among other protocols.

In certain embodiments, the subject extended transdermal delivery devices may be configured to deliver 75% or greater of the buprenorphine in the buprenorphine composition. In other words, the utilization percentage of buprenorphine from the extended transdermal delivery device is 75% or greater during the time the device is employed (e.g., over a predetermined dosage interval). As such, in these embodiments 25% or less of the original amount of buprenorphine remains in the transdermal buprenorphine composition after application. In certain embodiments, extended transdermal delivery devices are configured to deliver all of the buprenorphine composition. Therefore, the subject extended transdermal delivery devices are capable of high utilization percentage. In other words, the subject extended transdermal delivery devices are capable of delivering buprenorphine transdermally leaving little residual buprenorphine in the extended transdermal delivery device after a predetermined dosage interval. For instance, the subject extended transdermal delivery devices containing a buprenorphine composition having an amount of buprenorphine and an α-hydroxy acid may be configured to deliver 80% or greater of the buprenorphine in the transdermal composition, such as 85% or greater of the buprenorphine in the transdermal composition, such as 90% or greater of the buprenorphine in the transdermal composition, such as 95% or greater of the buprenorphine in the transdermal composition and including 99% or greater of the buprenorphine in the transdermal composition over the course of a predetermined dosage interval. For example, the dosage interval may be 7 days or longer. As such, the extended transdermal delivery device may be configured to deliver buprenorphine in a manner such that after 7 days or longer, 75% or greater of the buprenorphine is delivered, such as 80% or greater, such as 85% or greater, such as 90% or greater, such as 95% or greater and including 99% or greater of the buprenorphine in the transdermal composition is delivered after 7 days or longer. Put another way, extended transdermal delivery devices of interest may be configured such that buprenorphine utilized from the transdermal composition is 75% or greater during a predetermined dosage interval (e.g., 7 days or longer), such as 80% or greater, such as 85% or greater, such as 90% or greater, such as 95% or greater and including 99% or greater. Therefore, in these embodiments, the extended transdermal delivery device is configured such that 25% or less of the original amount of buprenorphine remains in the transdermal composition after usage.

For example, in some instances where the extended transdermal delivery device includes a buprenorphine composition which contains 10 mg of buprenorphine, the extended transdermal delivery device is configured to deliver 7.5 mg or more of buprenorphine in the transdermal buprenorphine composition over the course of the dosage interval (e.g., 7 days or longer), such as 8.0 mg or more, such as 8.5 mg or more, such as 9.0 mg or more, such as 9.5 mg or more and including 9.9 mg or more of buprenorphine in the transdermal composition. As such, 2.5 mg or less of buprenorphine remains in the transdermal buprenorphine composition after 7 days or longer, such as 2.0 mg or less, such as 1.5 mg or less, such as 1.0 mg or less and including 0.5 mg or less of buprenorphine remains in the transdermal buprenorphine composition after the dosage interval. In other instances, where the extended transdermal delivery device includes a buprenorphine composition which contains 7 mg of buprenorphine, the extended transdermal delivery device is configured to deliver 5.25 mg or more of buprenorphine in the transdermal composition, such as 5.5 mg or more, such as 6.0 mg or more, such 6.5 mg or more and including 6.9 mg or more of buprenorphine in the transdermal composition. As such, 1.75 mg or less of buprenorphine remains in the transdermal buprenorphine composition after the predetermined dosage interval (e.g., 7 days or longer), such as 1.5 mg or less, such as 1.25 mg or less, such as 1.0 mg or less and including 0.5 mg or less of buprenorphine remains in the transdermal buprenorphine composition after the predetermined dosage interval. In yet other instances, where the extended transdermal delivery device includes a buprenorphine composition which contains 4 mg of buprenorphine, the extended transdermal delivery device is configured to deliver 3 mg or more of buprenorphine in the transdermal composition, such as 3.1 mg or more, such as 3.2 mg or more, such 3.3 mg or more and including 3.4 mg or more of buprenorphine in the transdermal composition. As such, 1 mg or less of buprenorphine remains in the transdermal buprenorphine composition after the predetermined dosage interval (e.g., 7 days or longer), such as 0.9 mg or less, such as 0.8 mg or less, such as 0.7 mg or less and including 0.5 mg or less of buprenorphine remains in the transdermal buprenorphine composition after the predetermined dosage interval. In certain embodiments, extended transdermal delivery devices of interest include a transdermal buprenorphine composition having an amount of buprenorphine, an α-hydroxy acid and an polyisobutylene adhesive, where the extended transdermal delivery device is configured to deliver 75% or greater of the buprenorphine in the buprenorphine composition. For example, the subject extended transdermal delivery device may be configured to deliver 90% or more of the buprenorphine over the course of seven days or longer when the transdermal buprenorphine composition includes 10% w/w or less buprenorphine. Likewise, the subject extended transdermal delivery device may be configured to deliver 90% or more of the buprenorphine over the course of seven days or longer when the transdermal buprenorphine compositions has a molar ratio of α-hydroxy acid to buprenorphine ratio that is 2 or greater. As discussed above, in these embodiments, the transdermal buprenorphine composition may be a single layer matrix incorporating each of the buprenorphine, α-hydroxy acid and polyisobutylene adhesive as well as any other additional components into a single layer.

The term "dosage interval" is used herein to refer in its conventional sense to the duration of a single administration of the extended transdermal delivery device. In other words, a dosage interval begins with applying the transdermal buprenorphine composition to the skin or mucous membrane and ends with the removal of the transdermal buprenorphine composition from contact with the skin or mucous membrane. As such, a dosage interval may last about 24 hours or longer, such as about 48 hours or longer, such as about 72 hours or longer, such as 96 hours or longer, such as 120 hours or longer, such as 144 hours or longer and including about 168 hours or longer. The term "treatment regimen" as used herein refers to one or more sequential dosage intervals sufficient to produce the desired therapeutic effect of transdermal buprenorphine composition. Treatment regimens may include one or more dosage intervals, as desired, such as two or more dosage intervals, such as five or more dosage intervals, including ten or more dosage intervals.

In other embodiments, extended transdermal delivery devices having an amount of buprenorphine, an α-hydroxy acid and a pressure sensitive adhesive may be configured to deliver an average cumulative amount of buprenorphine of 60 $\mu g/cm^2$ or greater over an extended period of time. The term "cumulative amount" is meant the total quantity of buprenorphine delivered by the extended transdermal delivery device. In these embodiments, extended transdermal delivery devices of interest may be configured to deliver an average cumulative amount of buprenorphine may be 60 $\mu g/cm^2$ or greater, such as 75 $\mu g/cm^2$ or greater, such as 100 $\mu g/cm^2$ or greater over a 7 day delivery interval, such as 125 $\mu g/cm^2$ or greater, such as 150 $\mu g/cm^2$ or greater, such as 175 $\mu g/cm^2$ or greater and including 200 $\mu g/cm^2$ over a predetermined dosage interval.

In certain instances, the subject extended transdermal delivery devices are configured to deliver an average cumulative amount of buprenorphine of 60 $\mu g/cm^2$ or greater where buprenorphine is present in the transdermal buprenorphine composition in an amount which is 10% or less by weight of the total weight of the transdermal buprenorphine composition, such as 8% or less by weight, such as 6% or less by weight and including 4% or less by weight of the total weight of the transdermal buprenorphine composition. For example, in some instances, the extended transdermal delivery device is configured to deliver an average cumulative amount of buprenorphine ranging from 80 $\mu g/cm^2$ to 120 $\mu g/cm^2$ where buprenorphine is present in the transdermal buprenorphine composition in an amount which is 4% buprenorphine or less by weight. In other instances the extended transdermal delivery device is configured to deliver an average cumulative amount of buprenorphine ranging from 150 $\mu g/cm^2$ to 200 $\mu g/cm^2$ where buprenorphine is present in the transdermal buprenorphine composition in an amount which is 10% buprenorphine or less by weight.

In other instances, the subject extended transdermal delivery devices are configured to deliver an average cumulative amount of buprenorphine of 60 $\mu g/cm^2$ or greater where the weight ratio of α-hydroxy acid is 50% or less than the weight ratio of buprenorphine. For example, where the weight ratio of buprenorphine is 10% by weight of the total weight of the transdermal buprenorphine composition, the weight ratio of α-hydroxy acid is 5% by weight or less of the total weight of the transdermal buprenorphine composition, such as 4% by weight or less, such as 3% by weight or less and including 2% by weight or less of the total weight of the transdermal buprenorphine composition. In certain embodiments, extended transdermal delivery devices of interest include a transdermal buprenorphine composition having an amount of buprenorphine, an α-hydroxy acid and an acrylic adhesive, where the weight ratio of α-hydroxy acid is 50% or less than the weight ratio of buprenorphine. In these embodiments, the transdermal buprenorphine composition may be a single layer matrix incorporating each of the buprenorphine, α-hydroxy acid and an acrylic adhesive as well as any other additional components into a single layer.

In yet other instances, the subject extended transdermal delivery devices are configured to deliver an average cumulative amount of buprenorphine of 60 $\mu g/cm^2$ or greater where the molar ratio of α-hydroxy acid to buprenorphine is 2 or greater, such as 5 or greater.

In some embodiments, extended transdermal delivery devices of interest may include transdermal delivery devices having an amount of buprenorphine, an α-hydroxy acid and a pressure sensitive adhesive that are configured in a manner sufficient to deliver a predetermined buprenorphine dosage. The term "predetermined buprenorphine dosage" is meant the desired amount of buprenorphine to be delivered from the transdermal buprenorphine composition. For example, extended transdermal delivery devices may be configured in a manner sufficient to deliver a predetermined buprenorphine dosage of 5 $\mu g/hr$ or greater, such as 10 $\mu g/hr$ or greater, such as 20 $\mu g/hr$ or greater, such as 25 $\mu g/hr$ or greater, such as 30 $\mu g/hr$ or greater, such as 35 $\mu g/hr$ or greater, such as 45 $\mu g/hr$ or greater, such as 50 $\mu g/hr$ or greater and including 60 $\mu g/hr$ or greater. In certain embodiments, the extended transdermal delivery device may be configured in a manner sufficient to deliver a predetermined buprenorphine dosage ranging from 20 to 75 $\mu g/hr$, such as 21 to 70 µg/hr, such as 22 to 65 µg/hr, such as 23 to 60 µg/hr, such as 24 to 55 µg/hr, such as 25 to 50 µg/hr and including 28 to 48 µg/hr.

Depending on the desired therapeutic effect of the transdermal buprenorphine composition, the subject extended transdermal delivery devices may be configured to deliver a predetermined buprenorphine dosage as desired. In certain embodiments, the predetermined buprenorphine dosage in extended transdermal delivery device of interest is an amount which is in the "therapeutic window" of a subject, such as a human being. The term "therapeutic window" is used herein in its conventional sense to refer to the dosage range which is considered to be therapeutically effective for a particular drug. A therapeutically effective amount is an amount that when applied to a subject provides for a desired therapeutic activity.

Extended transdermal delivery devices of interest may also include devices having an amount of buprenorphine, an α-hydroxy acid and a pressure sensitive adhesive that are configured to provide a transdermal buprenorphine flux for an extended period of time which is within 90% or greater of peak transdermal buprenorphine flux when measured by an in-vitro protocol, such as for example protocols employing human cadaver skin with epidermal layers (stratum corneum and epidermis) in a Franz cell having donor and receptor sides clamped together and receptor solution containing phosphate buffer. By providing transdermal buprenorphine flux for an extended period of time which is within 90% of peak transdermal buprenorphine flux is meant that the extended transdermal delivery device is configured to provide a delivery rate of buprenorphine that does not decrease below 90% of the peak buprenorphine flux after reaching the peak flux as determined by an in-vitro protocol. In other words, the subject extended transdermal delivery device continues to maintain a constant average buprenorphine flux which is within 90% of the peak buprenorphine flux. For example, the extended transdermal delivery device is configured to maintain buprenorphine flux which is within 95% or more of peak transdermal buprenorphine flux, such as within 96% or more, such as within 97% or more, such as within 98% and including within 99% of peak transdermal buprenorphine flux after reaching peak transdermal flux. In certain embodiments, the extended transdermal delivery device is configured to maintain a buprenorphine flux which does not decrease at all after reaching peak flux and maintains a rate of 100% of peak buprenorphine flux. In certain embodiments, extended transdermal delivery devices of interest include a transdermal buprenorphine composition having an amount of buprenorphine, an α-hydroxy acid and an acrylic adhesive, where the extended transdermal delivery device is configured to provide a transdermal buprenorphine flux for an extended period of time which is within 90% or greater of peak transdermal buprenorphine flux when measured by an in-vitro protocol. In these embodiments, the transdermal buprenorphine composition may be a single layer matrix incorporating each of the buprenorphine, α-hydroxy acid and acrylic adhesive as well as any additional components into a single layer.

The flux of an active agent by transdermal administration is the rate of penetration of the active agent, such as when determined by an in-vitro protocol, for example by protocols employing human cadaver skin with epidermal layers (stratum corneum and epidermis) in a Franz cell having donor and receptor sides clamped together and receptor solution containing phosphate buffer. For instance, the flux of buprenorphine can be determined by the equation:

$$J_{skin\ flux} = P \times C \quad (1)$$

where J is the skin flux, C is the concentration gradient across the skin or mucous membrane and P is the permeability coefficient. Skin flux is the change in cumulative amount of drug passing across the skin or mucous membrane with respect to time.

As such, the subject extended transdermal delivery devices are configured to provide a steady state average flux of buprenorphine when determined by an in-vitro protocol (e.g., using cadaver skin in a Franz cell). The term "steady state" is used in its conventional sense to mean that extended transdermal delivery device can deliver a substantially constant amount of buprenorphine. By "substantially constant" is meant the buprenorphine flux increases or decreases by 10% or less at any time while in use, such as 8% or less, such as 7% or less, such as 6% or less, such as 5% or less, such as 3% or less, such as 2.5% or less, such as 2% or less, and including 1% or less at any time while in use. In other words, extended transdermal delivery devices of interest may be configured in a manner sufficient to deliver a "zero-order" buprenorphine flux after reaching peak buprenorphine flux.

The peak buprenorphine flux achieved by the subject extended transdermal delivery devices may vary, such as 0.5 µg/cm$^2$/hr or greater, such as 0.6 µg/cm$^2$/hr or greater, such as 0.65 µg/cm$^2$/hr or greater, such as 0.75 µg/cm$^2$/hr, such as 0.9 µg/cm$^2$/hr, such as 1.0 µg/cm$^2$/hr or greater, such as 1.5 µg/cm$^2$/hr or greater, such as 1.75 µg/cm$^2$/hr or greater and including peak flux of 2.0 µg/cm$^2$/hr or greater.

Extended transdermal delivery devices of interest may also include transdermal delivery devices having an amount of buprenorphine, an α-hydroxy acid and a pressure sensitive adhesive that are configured to deliver buprenorphine at a substantially linear rate over a predetermined dosage interval (e.g., 7 days or longer). By "substantially linearly" is meant that the cumulative amount of buprenorphine released from the transdermal buprenorphine composition increases at a substantially constant rate (i.e., defined by first-order kinetics). As such, the change in rate of cumulatively delivered buprenorphine increases or decreases by 10% or less at any given time, such as 8% or less, such as 7% or less, such as 6% or less, such as 5% or less, such as 3% or less, such as 2.5% or less, such as 2% or less, and including 1% or less.

In these embodiments, the extended transdermal delivery device is configured to provide a constant flux, such as by providing an excess of the buprenorphine transdermal composition in the extended transdermal delivery device. For example, an excess in buprenorphine may be a 5% or greater excess of the predetermined buprenorphine dosage, such as a 10% excess or greater, such as a 15% excess or greater, such as a 20% excess or greater, and including a 25% excess or greater of the predetermined buprenorphine dosage. Where an excess in predetermined buprenorphine dosage is employed in order to provide a constant flux, the excess amount is not absorbed during administration of the extended transdermal delivery device.

Methods for Applying Extended Buprenorphine Transdermal Delivery Devices Containing Buprenorphine Compositions Methods of using the subject extended transdermal delivery devices include administering an effective amount of the transdermal buprenorphine composition to a subject in order to treat a subject for a target condition of interest, e.g., treating pain as described in greater detail below. By "treating" or "treatment" is meant at least a suppression or amelioration of the symptoms associated with the condition affecting the subject, where suppression and amelioration are used in a broad sense to refer to at least a reduction in the magnitude of a parameter, e.g., symptom, associated with the condition being treated. As such, treatment also includes situations where the condition is completely inhibited, e.g., prevented from happening, or stopped, e.g., terminated, such that the subject no longer experiences the condition. As such, treatment includes both preventing and managing a condition.

In certain embodiments, the subject extended transdermal delivery devices as described herein are used in the treatment or prevention of pain. The term "pain" is used in its conventional sense to refer to the unpleasant sensory and emotional experience associated with actual or potential tissue damage, or described in terms of such damage (e.g., as defined by the International Association for the Study of Pain). Pain may also involve unpleasant sensory and emotional experience where the damage is not clearly located or cannot be shown to exist. In certain instances, pain includes any sensory experience that causes suffering (physical, psychological, emotional, mental, etc.) in a subject. Pain indications according to embodiments of the invention may include, but are not limited to neuralgia such as trigeminal neuralgia, myalgia, hyperalgesia, hyperpathia, neuritis, neuropathy, neuropathic pain, idiopathic pain, acute pain, sympathetically mediated pain, complex regional pain, chronic pain, such as cancer pain, post-operative pain, post-herpetic neuralgia, irritable bowel syndrome and other visceral pain, radiation pain, diabetic neuropathy, pain associated with muscle spasticity, complex regional pain syndrome (CRPS), sympathetically maintained pain, headache pain including migraine headaches, allodynic pain, inflammatory pain, such as pain associated with arthritis, gastrointestinal pain, such as irritable bowel syndrome (IBS) and Crohn's disease. Pain according to some embodiments, may be a symptom of an underlying physiological abnormality, such as cancer, arthritis, viral infection such as herpes zoster, or physical trauma such as a burn, injury or surgery, chemotherapy-induced pain, painful chronic chemotherapy induced peripheral neuropathy (CCIPN), radiation therapy pain.

In certain embodiments, the pain condition is neuropathic pain. The term "neuropathic pain" is used in it conventional sense to refer to pain caused by damage or disease that affects the somatosensory system. Neuropathic pain may be associated with paresthesia, dysesthesia, hypoesthesia, hyperesthesia, hypoalgesia, hyperalgesia, or allodynia or other related phenomena. Neuropathic pain may be continuous or episodic. Neuropathic pain suitable for management with the subject methods may be any type of neuropathic pain and includes but is not limited to postherpetic neuralgia, trigeminal neuralgia, HIV-distal sensory polyneuropathy, diabetic neuropathy, traumatic nerve injury, post-surgical pain, chemotherapy-induced pain, painful chronic chemotherapy induced peripheral neuropathy (CCIPN), radiation therapy pain, sports injury, pain associated with stroke, multiple sclerosis, syringomyelia, epilepsy, spinal cord injury, cancer, phantom limb pain, carpal tunnel syndrome, sciatica, pudendal neuralgia, central pain syndrome, headache, migraine, backaches, chronic back pain, fibromyalgia, among other types of neuropathic pain.

In some instances, embodiments provide a method of treating pain. In other instances, embodiments provide a method of preventing pain, such as, by prophylactically administering one or more of the subject extended transdermal delivery devices.

In practicing the methods, the extended transdermal delivery devices containing buprenorphine compositions disclosed herein can be topically administered to a subject, i.e., the extended transdermal delivery devices may be administered to any convenient topical site for which an active agent (i.e., drug) may be delivered into the subject As such, transdermal buprenorphine compositions as described herein may be delivered to the subject through one or more of the subcutis, dermis and epidermis, including the stratum corneum, stratum germinativum, stratum spinosum and stratum basale. Topical sites of interest include, but are not limited to the mucosal or keratinized sites of the arms, legs, buttocks, abdomen, back, neck, scrotum, vagina, face, behind the ear, buccally as well as sublingually. The surface area that is covered by the topical composition following application is sufficient to provide for the desired amount of agent administration, and in some embodiments ranges from 1 to 200 $cm^2$, such as from 10 to 180 $cm^2$, and including from 100 to 150 $cm^2$, e.g., 140 $cm^2$.

The subject extended transdermal delivery devices may be applied and maintained at the application site over an extended period of time, as desired to deliver a desired amount of buprenorphine. For example, the extended transdermal delivery device may be maintained at the application site over the course of hours, days and including weeks. In some embodiments, sustained release transdermal administration of the buprenorphine composition includes multi-day delivery of a therapeutically effective amount of the buprenorphine active agent that is topically applied to the skin of a subject. As described in detail above, the transdermal composition may be formulated to provide a therapeutically effective amount of buprenorphine when the extended transdermal delivery device is applied to the skin of a subject for a period of time that is 1 day or longer, such as 2 days or longer, such as 3 days or longer, such as 5 days or longer, such as 7 days or longer, including 10 days or longer. In certain embodiments, extended transdermal delivery devices provided by the present invention provide a therapeutically effective amount of buprenorphine to a subject for a period of 7 days or longer.

In practicing the subject methods, a given dosage of the transdermal composition may be applied a single time or a plurality of times over a given time period, e.g., the course of the disease condition being treated, where the dosing schedule when a plurality of compositions are administered over a given time period may be daily, weekly, biweekly, monthly, etc. For example, the subject methods include multiple dosage intervals. By "multiple dosage intervals" is meant more than one extended transdermal delivery device is applied and maintained in contact with the subject in a sequential manner. As such, a first extended transdermal delivery device is removed from contact with the subject and a second extended transdermal delivery device is reapplied to the subject. In practicing methods of the invention, treatment regimens may include two or more dosing intervals, such as three or more dosing intervals, such as four or more dosing intervals, such as five or more dosing intervals, including ten or more dosing intervals.

The duration between dosage intervals in a multiple dosage interval treatment regimen may vary, as determined by a qualified health care professional. For example, the duration between dosage intervals in a multiple dosage treatment regimen may be predetermined and follow at regular intervals. As such, the time between dosing intervals may vary and may be 1 day or longer, such as 2 days or longer, such as 3 days or longer, such as 4 days or longer, such as 5 days or longer, such as 6 days or longer, such as 7 days or longer, such as 10 days or longer, including 30 days or longer.

The location on the subject for reapplying subsequent extended transdermal delivery devices in multiple dosage treatment regimens may be the same or different from the location on the subject where the previous extended transdermal delivery device was removed. In some instances, the second or subsequent extended transdermal delivery device is applied to a different skin site to reduce the possible occurrence of skin irritation and/or skin sensitization at the prior site of application.

For example, if a first extended transdermal delivery device is applied and maintained on the leg of the subject, one or more subsequent extended transdermal delivery devices may be reapplied to the same position on the leg of the subject. On the other hand, if a first extended transdermal delivery device was applied and maintained on the leg of the subject, one or more subsequent extended transdermal delivery device may be reapplied to a different position, such as the abdomen or back of the subject. Subsequent dosages applied in multiple dosage interval regimens may have the same or different formulation of buprenorphine. In certain instances, a subsequent dosage interval in a treatment regimen may contain a higher or lower concentration of buprenorphine than the previous dosage interval. For example, the concentration of buprenorphine may be increased in subsequent dosage intervals by 10% or greater, such as 20% or greater, such as 50% or greater, such as 75% or greater, such as 90% or greater and including 100% or greater. On the other hand, the concentration of buprenorphine may be decreased in subsequent dosage intervals, such as by 10% or greater, such as 20% or greater, such as 50% or greater, such as 75% or greater, such as 90% or greater and including 100% or greater.

In other instances, a subsequent dosage interval may contain a different formulation of buprenorphine than the previous dosage interval, such as a different α-hydroxy acid, pressure sensitive adhesive, weight ratio of α-hydroxy acid to buprenorphine or molar ratio of buprenorphine to α-hydroxy acid, as described in detail above.

The area of skin covered by the topical composition when applied may vary. In some instances, the area of skin covered by the topical composition upon application ranges from 1 to 200 cm$^2$, such as 10 to 180 cm$^2$ and including 100 to 150 cm$^2$.

In certain embodiments, the subject methods include diagnosing a subject as in need of treatment with one or more of the subject extended transdermal delivery devices described above. Individuals may be diagnosed using any convenient protocol. In addition, individuals may be known to be in need of the subject methods, e.g., they are suffering from pain such as cancer pain, orthopedic pain, muscular pain, topical pain, pain associated with trauma or surgery and neurological pain, among other types of pain. Diagnosis or assessment of target condition can be performed using any convenient diagnostic protocol as determined by a qualified health care professional.

In certain embodiments, methods of the invention provide for prophylactically administering one or more of the subject extended transdermal delivery devices described above, such as for example before planned surgery. The composition may be applied prophylactically as desired, such as one hour or more prior to a planned procedure, such as 1 hours prior to a planned procedure, such as 2 hours prior to a planned procedure, and including 10 hours prior to a planned procedure.

In certain embodiments, the subject buprenorphine transdermal composition can be administered prior to, concurrent with, or subsequent to other therapeutic agents, such as for example, for treating or managing pain. If provided at the same time as another therapeutic agent, the subject buprenorphine compositions may be administered in the same or in a different composition. Thus, buprenorphine compositions of interest and other therapeutic agents can be administered to the subject by way of concurrent therapy. By "concurrent therapy" is intended administration to a subject such that the therapeutic effect of the combination of the substances is caused in the subject undergoing therapy. For example, concurrent therapy may be achieved by administering buprenorphine compositions of the invention and a pharmaceutical composition having at least one other agent, such as pain treatment compositions including but not limited to NSAIDS (aspirin, ibuprofen, naproxen, celecoxib, acetaminophen), cyclooxygenase inhibitors, opioids such as codeine, oxycodone, morphine, methadone and fentanyl, anesthetics, antidepressants, anticonvulsants, topical agents, cannabinoids, N-methyl-D-Asparate, neuromodulators among other which in combination make up a therapeutically effective dose, according to a particular dosing regimen. Administration of the separate pharmaceutical compositions can be performed simultaneously or at different times (i.e., sequentially, in either order, on the same day, or on different days), so long as the therapeutic effect of the combination of these substances is caused in the subject undergoing therapy.

Where buprenorphine according to the subject compositions is administered concurrently with a second therapeutic agent to treat pain, the weight ratio of buprenorphine to second therapeutic agent may range from 1:2 and 1:2.5; 1:2.5 and 1:3; 1:3 and 1:3.5 1:3.5 and 1:4; 1:4 and 1:4.5; 1:4.5 and 1:5; 1:5 and 1:10; and 1:10 and 1:25 or a range thereof. For example, the weight ratio of buprenorphine to second therapeutic agent may range between 1:1 and 1:5; 1:5 and 1:10; 1:10 and 1:15; or 1:15 and 1:25. Alternatively, the weight ratio of the second therapeutic agent to buprenorphine ranges between 2:1 and 2.5:1; 2.5:1 and 3:1; 3:1 and 3.5:1; 3.5:1 and 4:1; 4:1 and 4.5:1; 4.5:1 and 5:1; 5:1 and 10:1; and 10:1 and 25:1 or a range thereof. For example, the ratio of the second therapeutic agent buprenorphine may range between 1:1 and 5:1; 5:1 and 10:1; 10:1 and 15:1; or 15:1 and 25:1.

Depending on the second therapeutic agent being administered and the condition indicated, concurrent administration with buprenorphine may reduce the required administration amount of the second therapeutic agent. For example, concurrent administration with buprenorphine may reduce the amount of other opioid or analgesic required to effectively treat or manage pain, such as post-operative pain, chemotherapy-induced pain or radiation therapy induced pain. Concurrent administration with buprenorphine may reduce the required administration amount of the second therapeutic agent by 10% or more, such as 25% or more, such as 35% or more and including reducing the required administration amount of second therapeutic agent by 50% or more.

Utility

Methods for applying and maintaining a buprenorphine composition in contact with a subject according to methods of the present invention find use in any application where a subject would benefit from being transdermally administered buprenorphine. Extended transdermal delivery devices containing buprenorphine according to the present invention find use in the treatment or prevention of pain which originate from a variety of different sources or disease conditions, such as but not limited to: acute pain, chronic pain, neuropathic pain, acute traumatic pain, arthritic pain, osteoarthritic pain, rheumatoid arthritis pain, muscular skeletal pain, post dental surgical pain, dental pain, myofascial pain, cancer pain, visceral pain, diabetic pain, muscular pain, post herpetic neuralgic pain, chronic pelvic pain, endometriosis pain, pelvic inflammatory pain and child birth related pain. Acute pain includes, but is not limited to, acute traumatic pain or post-surgical pain. Chronic pain includes, but is not limited to, neuropathic pain, arthritic pain, osteoarthritic pain, rheumatoid arthritis pain, muscular skeletal pain, dental pain, myofascial pain, cancer pain, diabetic pain, visceral pain, muscular pain, post herpetic neuralgic pain, chronic pelvic pain, endometriosis pain, pelvic inflammatory pain and back pain. In some instances, embodiments provide a method of treating pain. In other instances, embodiments provide a method of preventing pain, such as, by prophylactically administering one or more of the subject extended transdermal delivery devices.

By treatment is meant that at least an amelioration of the symptoms associated with the condition afflicting the subject is achieved, where amelioration is used in a broad sense to refer to at least a reduction in the magnitude of a parameter, e.g., symptom, associated with the condition being treated. As such, treatment also includes situations where the pathological condition, or at least symptoms associated therewith, are completely inhibited, e.g., prevented from happening, or stopped, e.g., terminated, such that the subject no longer suffers from the condition, or at least the symptoms that characterize the condition.

Kits

Kits for use in practicing certain methods described herein are also provided. In certain embodiments, the kits include one or more extended transdermal delivery devices containing a buprenorphine composition having an amount of buprenorphine and α-hydroxy acid as described above. In certain embodiments, the kits include an adhesive overlay as described above. In a given kit that includes two or more of the subject extended transdermal delivery devices, the compositions may be individually packaged or present within a common container.

In certain embodiments, the kits will further include instructions for practicing the subject methods or means for obtaining the same (e.g., a website URL directing the user to a webpage which provides the instructions), where these instructions may be printed on a substrate, where substrate may be one or more of: a package insert, the packaging, reagent containers and the like. In the subject kits, the one or more components are present in the same or different containers, as may be convenient or desirable.

The following examples are offered by way of illustration and not by way of limitation. Specifically, the following examples are of specific embodiments for carrying out the present invention. The examples are for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

EXPERIMENTAL

Materials and Methods

Preparation of Example Buprenorphine Transdermal Formulations

Formulations were prepared by mixing stock solutions of each of the mixture components in organic solvents (typically 30-60 wt % solid content in ethyl acetate, isopropyl alcohol, hexane, or heptane), followed by mixing. Once a homogeneous mixture was formed, the solution was cast on a release liner (siliconized polyester sheet of 2-3 mils) and dried at 65°-80° C. for 10-90 minutes. The single layer adhesive films were then laminated to a PET backing, cut to the desired size, and pouched.

Transdermal Flux Tests

Human cadaver skin was used and epidermal layers (stratum corneum and epidermis) were separated from the full-thickness skin as skin membrane. Samples were die-cut with an arch punch to a final diameter of about 2.0 cm$^2$. The release liner was removed and the system was placed on top of the epidermis/stratum corneum with the drug adhesive layer facing the stratum corneum. Gentle pressure was applied to effect good contact between the adhesive layer and stratum corneum. The donor and receptor sides of the Franz cell were clamped together and the receptor solution containing a phosphate buffer at pH 6.5 was added to the Franz cell. The cells were kept at 33° C. for the duration of the experiment. Samples of the receptor solution were taken at regular intervals and the active agent concentration was measured by HPLC. The removed receptor solution was replaced with fresh solution to maintain the sink conditions. The flux was calculated from the slope of cumulative amounts of the drug in the receiver compartment versus time plot.

EXAMPLES

Example 1

Figure 2:
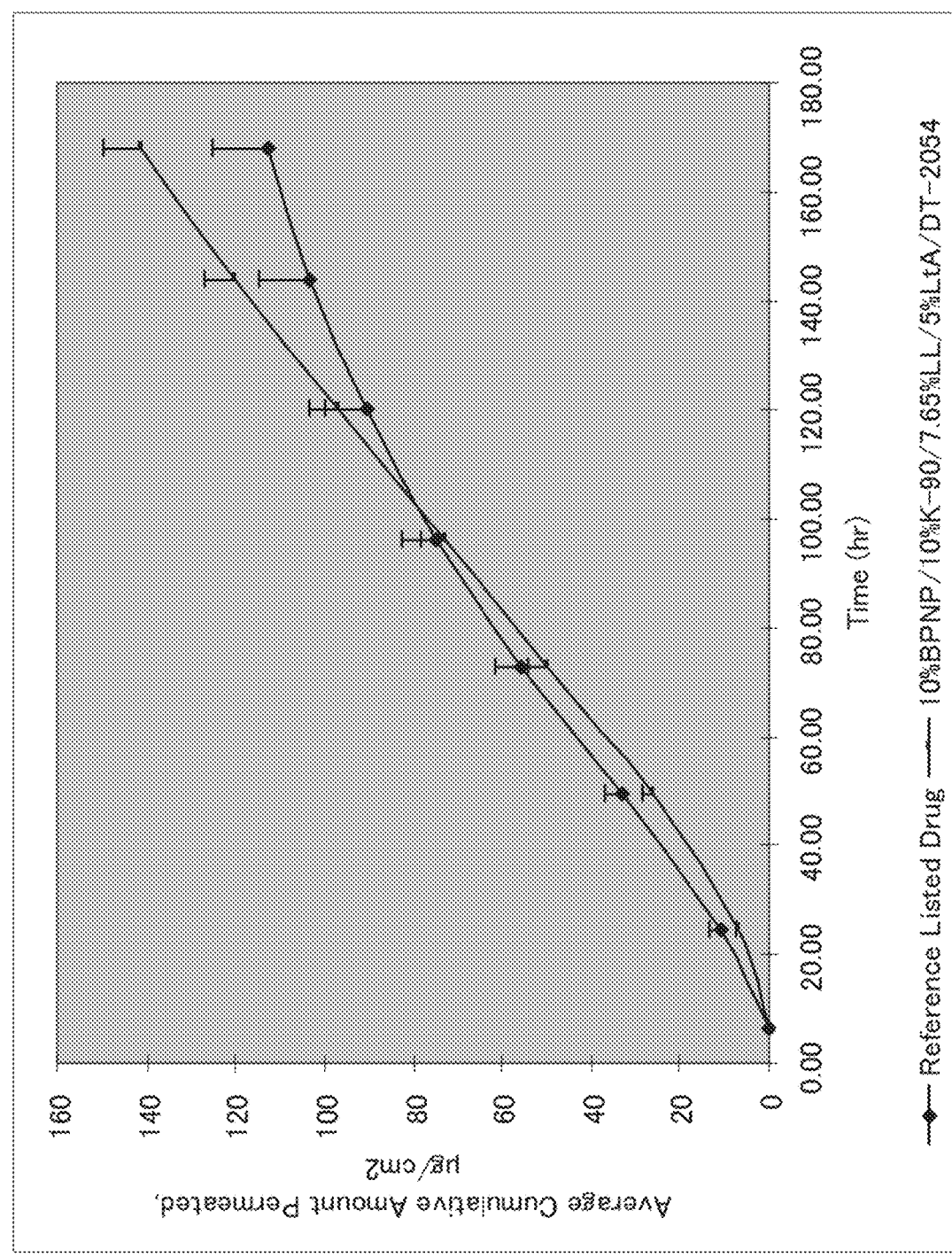
FIG. 2 shows an example of a plot of the average cumulative amount of buprenorphine permeated as a function of time for a transdermal composition applied for a 168 hour dosage interval according to one embodiment.

An example buprenorphine transdermal composition formulation is shown in Table 1. An in vitro skin flux study was performed as described above with an extended transdermal delivery device having a formulation shown in Table 1. The extended transdermal delivery device was compared with a Reference Listed Drug (RLD) which contains a weight ratio of buprenorphine that is equivalent to weight ratio of acid. The average buprenorphine flux rate and average amount of buprenorphine permeated with respect to time are illustrated in FIGS. 1 and 2. As depicted in FIG. 1, the transdermal buprenorphine flux is maintained at 90% or greater of peak transdermal buprenorphine flux until at least 7 days after reaching peak buprenorphine flux. The flux from the RLD, however, declines immediately after reaching peak buprenorphine flux.

TABLE 1

| Ingredients | % wt/wt |
| --- | --- |
| Buprenorphine base | 10.00 |
| PVP K 90 | 10.00 |
| Lactic acid | 5.00 |
| Lauryl lactate | 7.65 |
| Duro-tak 87-2054 | 67.35 |

Example 2

Figure 3:
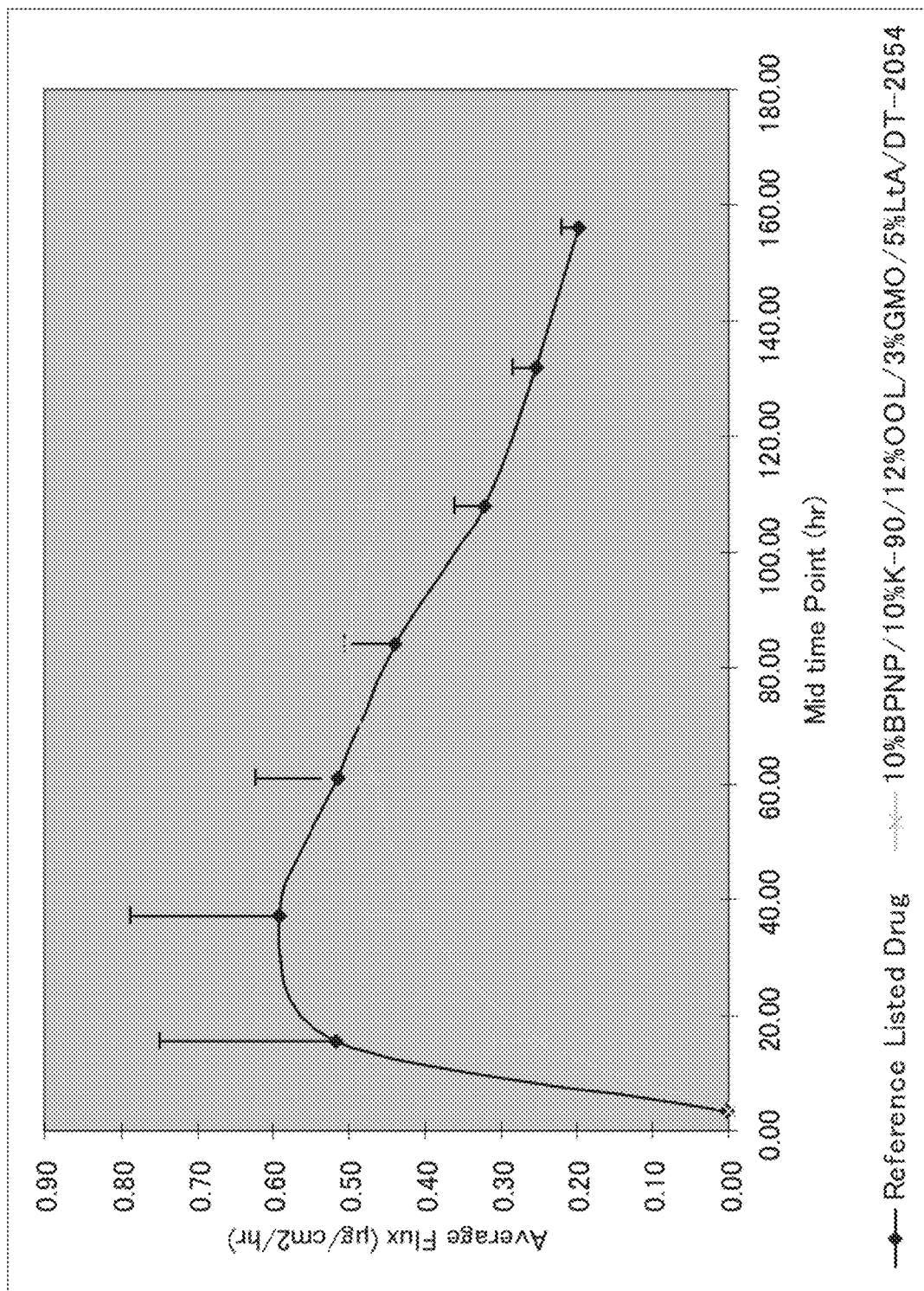
FIG. 3 shows an example of data acquired for determining average buprenorphine flux as a function of extended transdermal delivery device application time according to another embodiment.
Figure 4:
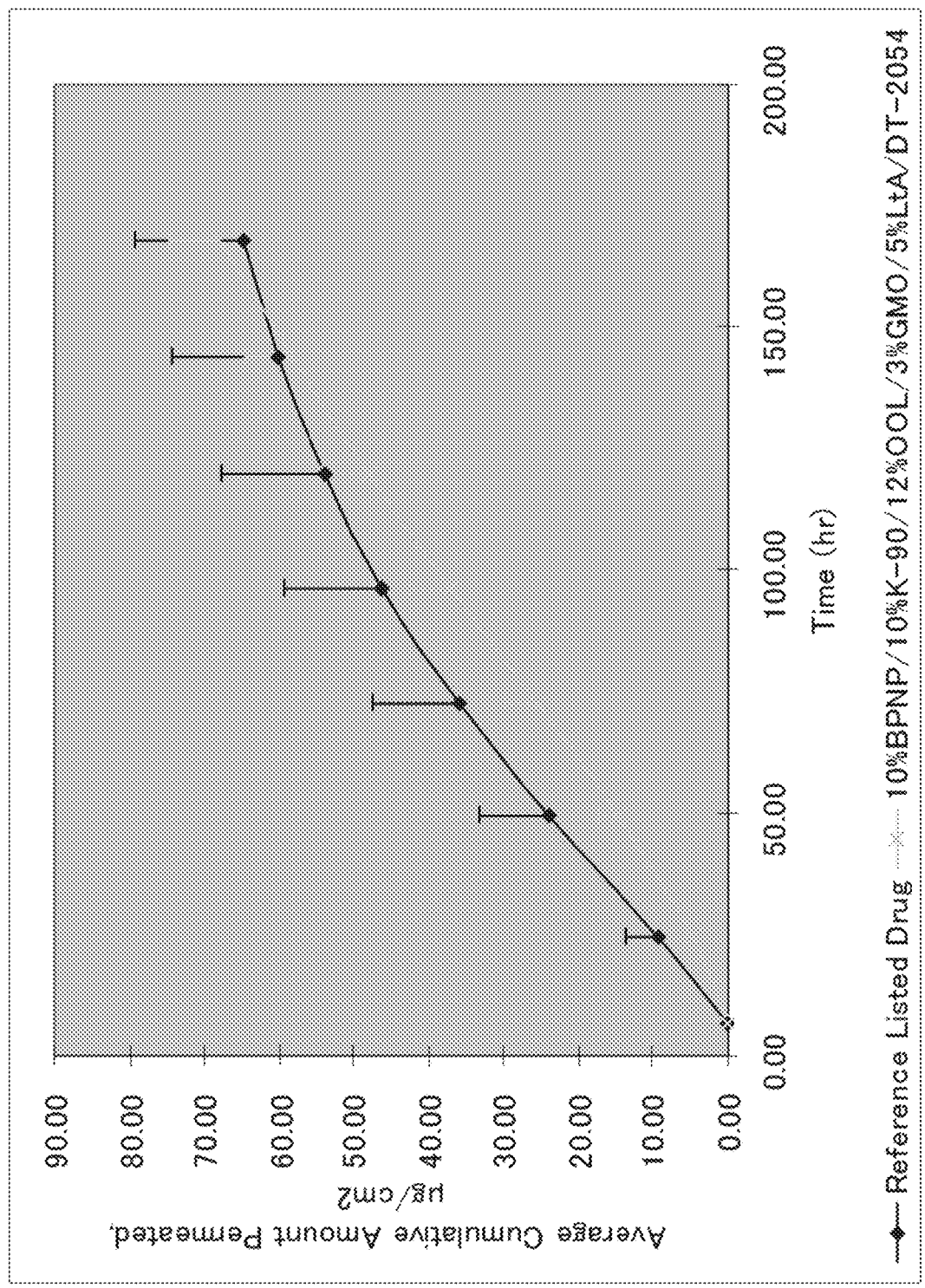
FIG. 4 shows an example of a plot of the average cumulative amount of buprenorphine permeated as a function of time for a transdermal composition applied for a 168 hour dosage interval according to another embodiment.

A second example buprenorphine transdermal composition formulation is shown in Table 2. An in vitro skin flux study was performed as described above with an extended transdermal delivery device having a formulation shown in Table 2. The extended transdermal delivery device was compared with a Reference Listed Drug (RLD) which contains a weight ratio of buprenorphine that is equivalent to weight ratio of acid. The average buprenorphine flux rate and average amount of buprenorphine permeated with respect to time are illustrated in FIGS. 3 and 4. As depicted in FIG. 3, the transdermal buprenorphine flux is maintained at 90% or greater of peak transdermal buprenorphine flux until at least 7 days after reaching peak buprenorphine flux. The flux from the RLD, however, declines immediately after reaching peak buprenorphine flux.

TABLE 2

| Ingredients | % wt/wt |
| --- | --- |
| Buprenorphine base | 10.00 |
| PVP K 90 | 10.00 |
| Lactic acid | 5.00 |
| Glyceryl monoleate (GMO) | 3.00 |
| Oleyl oleate | 12.00 |
| Duro-tak 87-2054 | 60.00 |

Example 3

Figure 5:
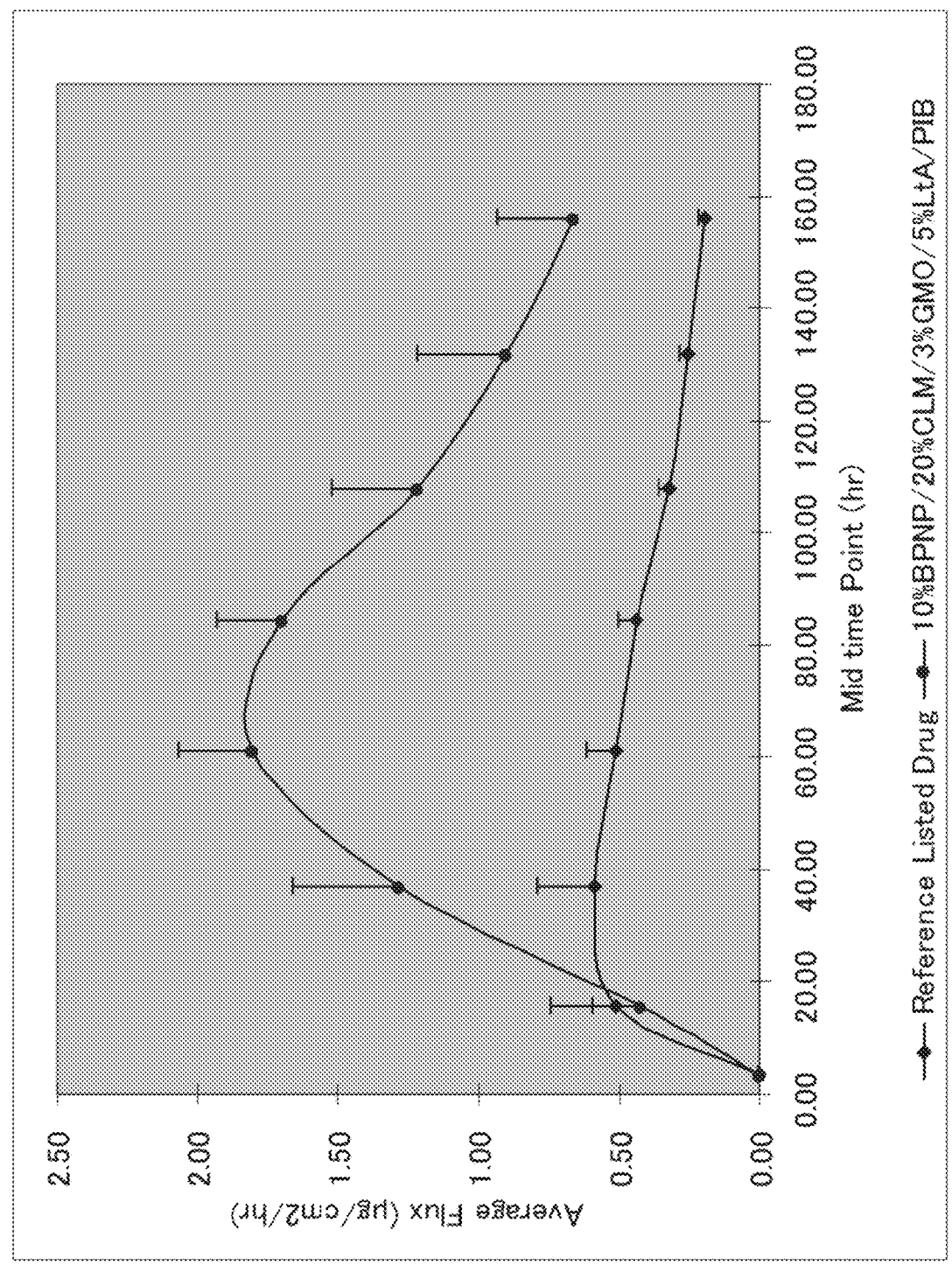
FIG. 5 shows an example of data acquired for determining average buprenorphine flux as a function of extended transdermal delivery device application time according to another embodiment.
Figure 6:
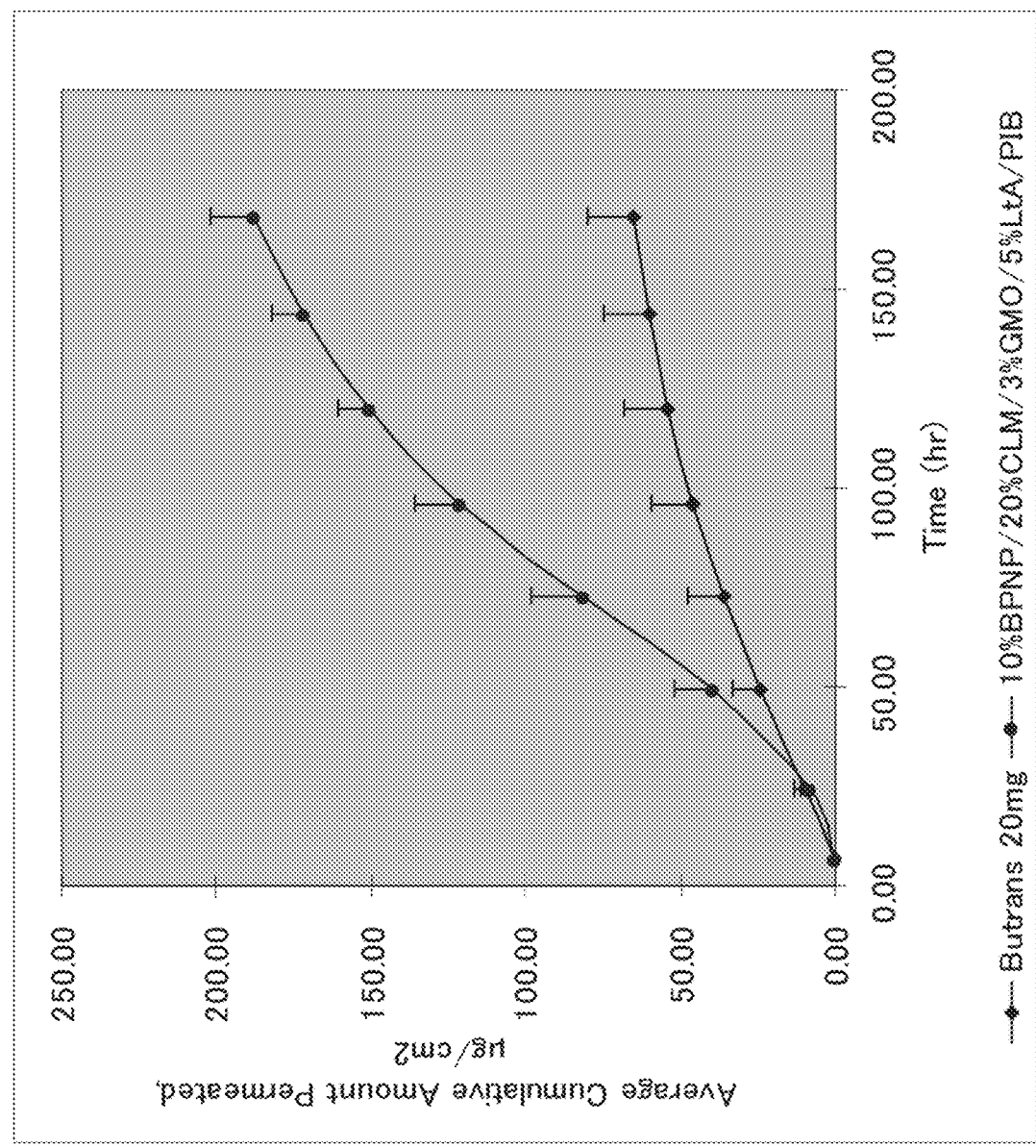
FIG. 6 shows an example of a plot of the average cumulative amount of buprenorphine permeated as a function of time for a transdermal composition applied for a 168 hour dosage interval according to another embodiment.

A third example buprenorphine transdermal composition formulation is shown in Table 3. The pressure sensitive adhesive used in this example is polyisobutylene/polybutene (PIB/PB) based adhesive as shown in Table 3. The extended transdermal delivery device was compared with a Reference Listed Drug (RLD) which contains a weight ratio of buprenorphine that is equivalent to the weight ratio of acid. The average buprenorphine flux rate and average amount of buprenorphine permeated with respect to time are illustrated in FIGS. 5 and 6. In vitro flux is higher from a PIB/PB based formulation than that of the RLD. Furthermore, total amount of buprenorphine delivered is almost 3 fold higher than the RLD. This result demonstrates that with the same size and drug content as the RLD, a higher buprenorphine dose of 1 to 1.4 mg/day can be delivered.

TABLE 3

| Ingredients | % wt/wt |
| --- | --- |
| Buprenorphine base | 10.00 |
| PVP CLM (crosslinked) | 20.00 |
| Lactic acid | 5.00 |
| Glyceryl monoleate (GMO) | 3.00 |
| PIB/PB mix | 62.00 |

Example 4

Figure 7:
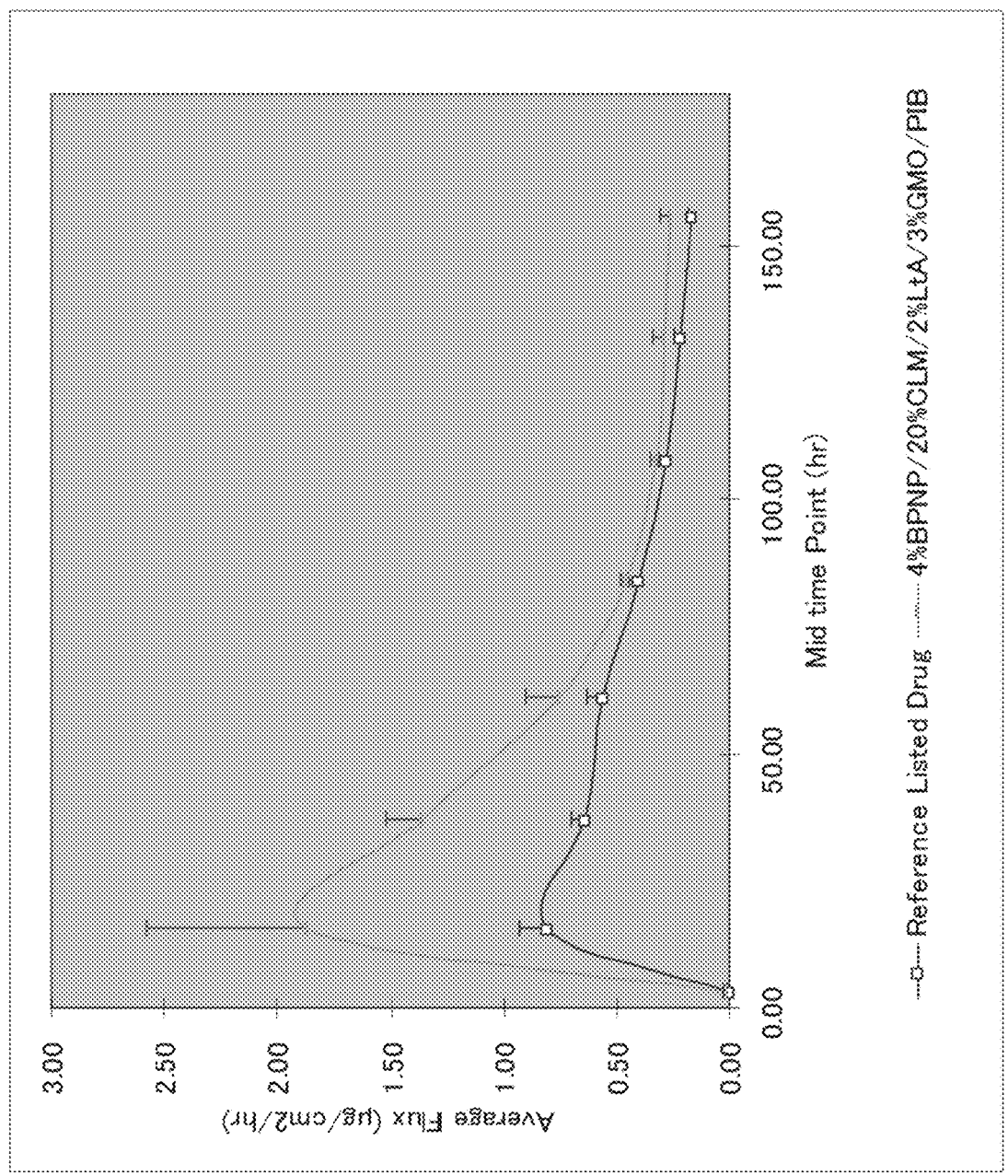
FIG. 7 shows an example of a plot of the average buprenorphine flux as a function of extended transdermal delivery device application time according to another embodiment.
Figure 8:
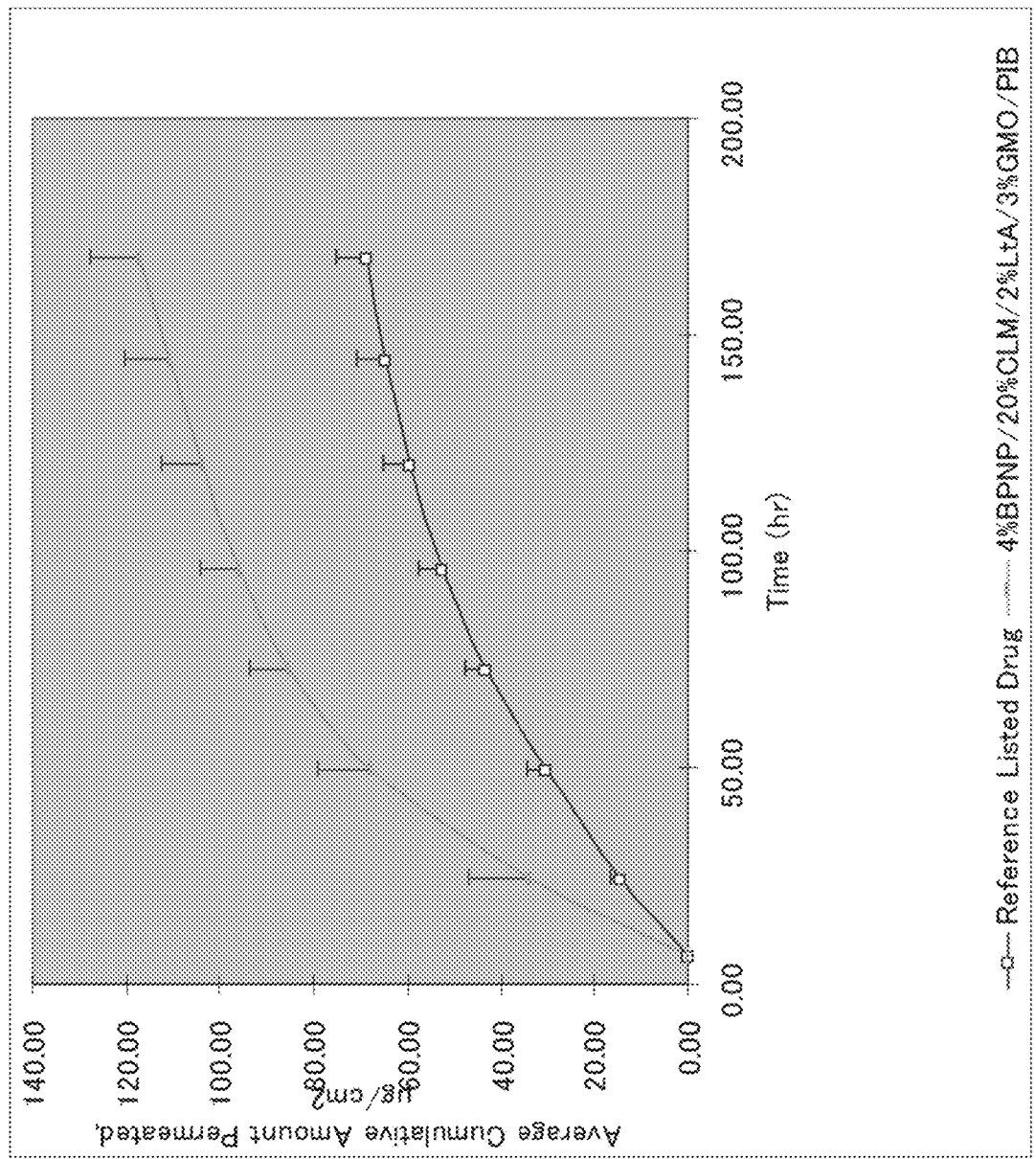
FIG. 8 shows an example of a plot of the average cumulative amount of buprenorphine permeated as a function of time for a transdermal composition applied for a 168 hour dosage interval according to another embodiment.

A fourth example buprenorphine transdermal composition formulation is shown in Table 4. The pressure sensitive adhesive used in this example is polyisobutylene/polybutene (PIB/PB) based adhesive as shown in Table 4. As depicted in FIGS. 7 and 8, with a buprenorphine transdermal composition having PIB/PB, 0.5 mg/day dose of buprenorphine can be delivered using a 4.0% by weight bupenorphine loading.

TABLE 4

| Ingredients | % wt/wt |
| --- | --- |
| Buprenorphine base | 4.00 |
| PVP CLM (crosslinked) | 20.00 |
| Lactic acid | 2.00 |
| Glyceryl monoleate (GMO) | 3.00 |
| PIB/PB mix | 71.00 |

Example 5

Figure 9:
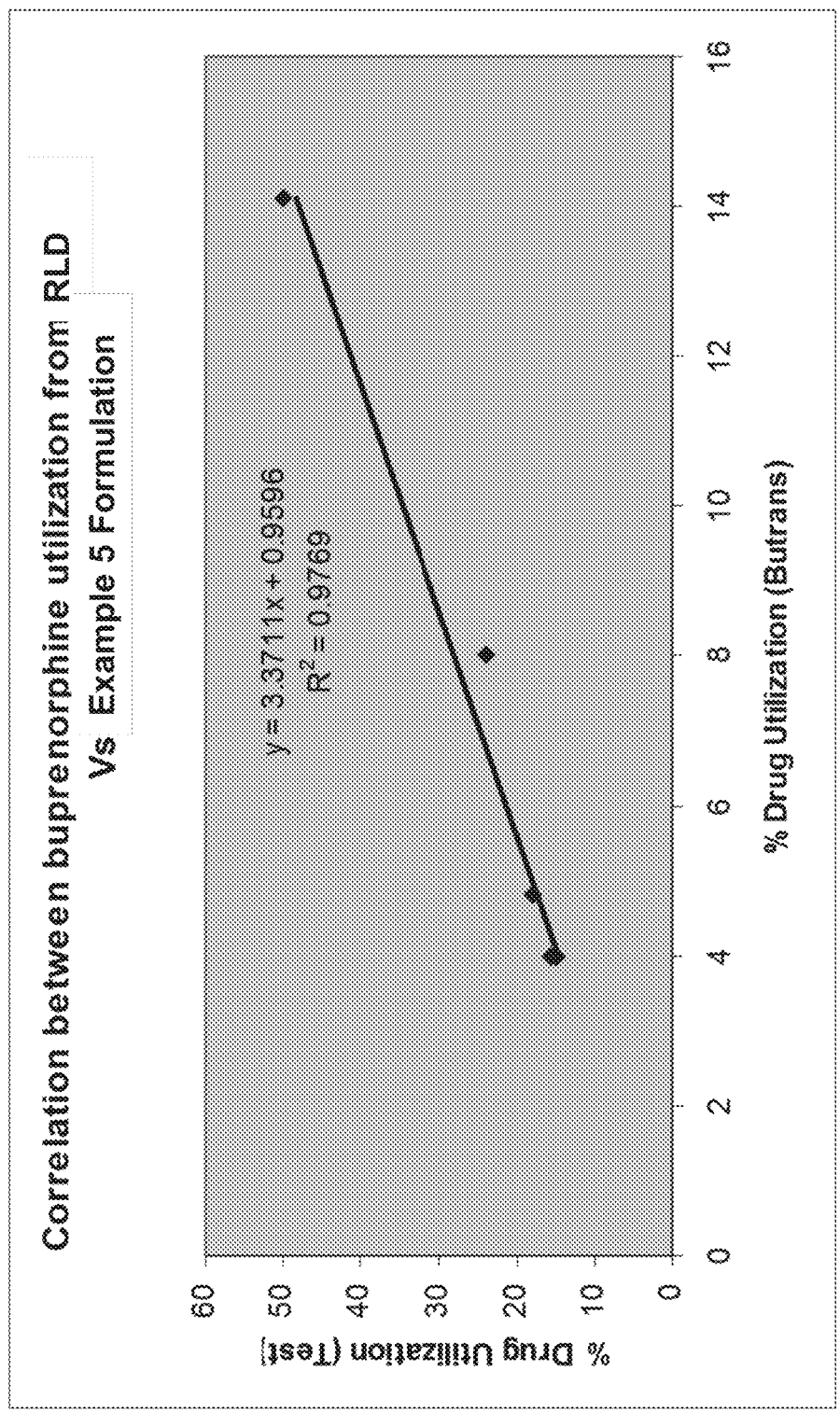
FIG. 9 shows a plot of the correlation between the buprenorphine utilization from an extended transdermal delivery device according to one embodiment of the present invention and from an Reference Listed Drug (RLD) device.

Buprenorphine utilization from the formulation described in Example 3 above is compared with a Reference Listed Drug. FIG. 9 shows the correlation between buprenorphine delivery from an extended transdermal delivery device having the buprenorphine transdermal composition formulation of Example 3 and the RLD. As illustrated, an extended transdermal delivery device having the buprenorphine transdermal composition formulation of Example 3 showed a 3-fold higher utilization than that of the RLD. This data was generated on 4 different skin donors which have different skin permeability.

Example 6

Figure 10:
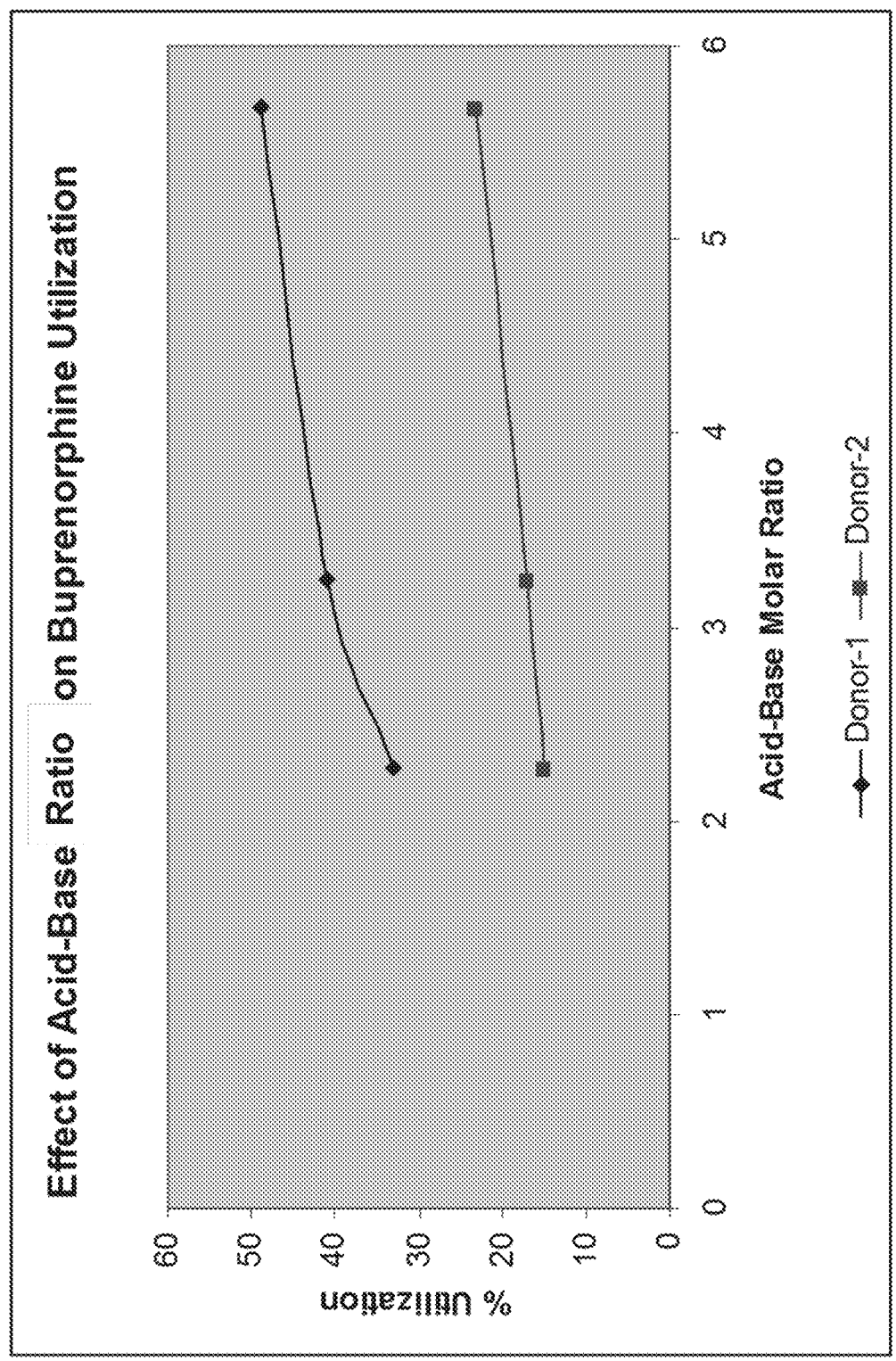
FIG. 10 shows a plot of the effect of acid-buprenorphine ratio on buprenorphine utilization from extended transdermal delivery devices according to certain embodiments of the present invention.
Figure 11:
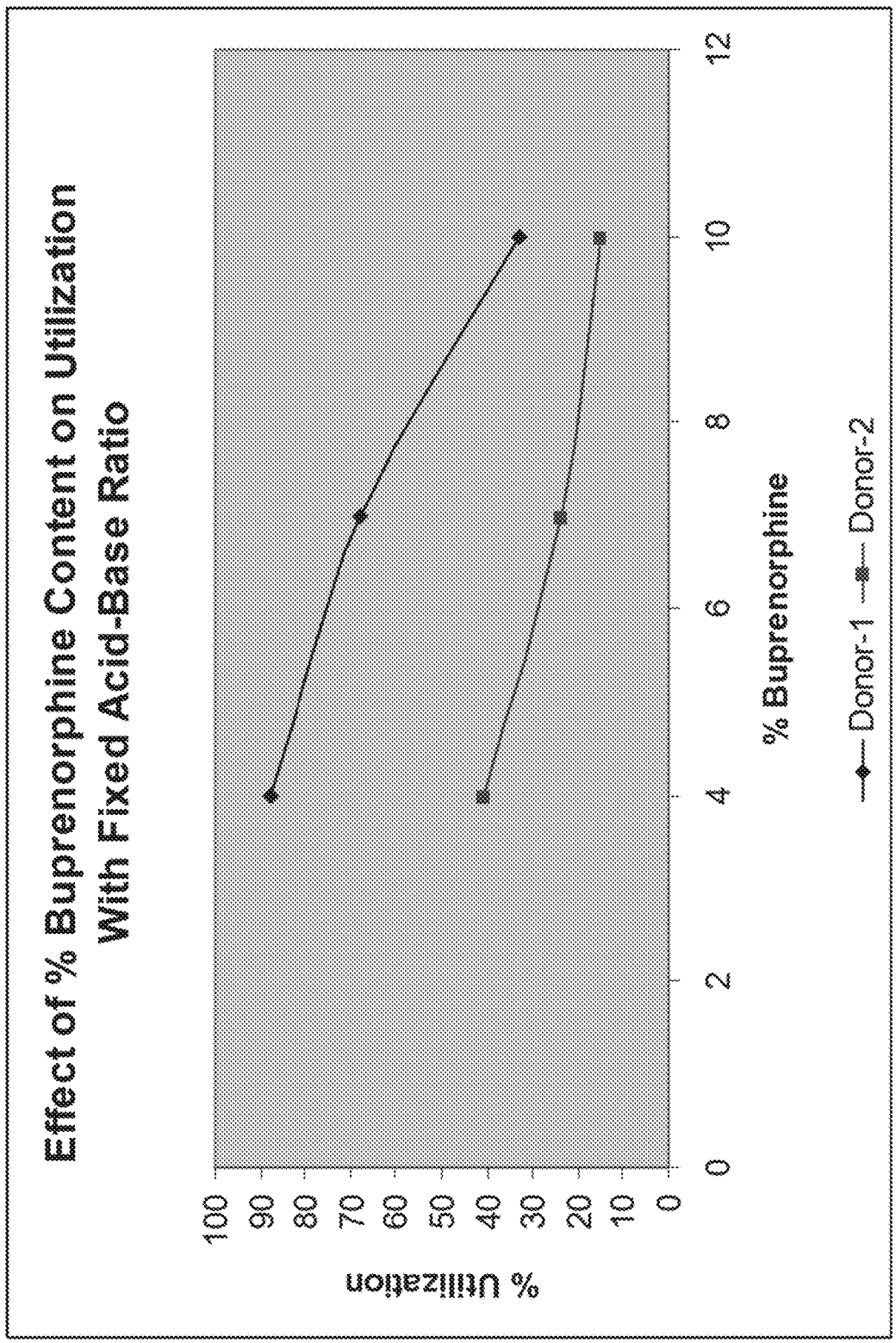
FIG. 11 shows a plot of the effect of buprenorphine content where the acid-buprenorphine ratio is fixed on buprenorphine utilization from extended transdermal delivery devices according to certain embodiments of the present invention.

The utilization of buprenorphine from extended transdermal delivery devices having varying ratios of acid to buprenorphine was studied. Table 5 summarizes five transdermal buprenorphine composition formulations having varying ratios of acid to buprenorphine. FIGS. 10 and 11 summarize the effect of acid-base ratio and % buprenorphine on buprenorphine utilization (i.e., in vitro delivery).

TABLE 5

| Ingredients | % wt/wt | | | | |
| --- | --- | --- | --- | --- | --- |
|  | 1 | 2 | 3 | 4 | 5 |
| Buprenorphine base | 4.00 | 7.00 | 10.00 | 4.00 | 7.00 |
| PVP CLM (crosslinked) | 20.00 | 20.00 | 20.00 | 20.00 | 20.00 |
| Lactic acid | 2.00 | 3.50 | 5.00 | 5.00 | 5.00 |
| Glyceryl monoleate (GMO) | 3.00 | 3.00 | 3.00 | 3.00 | 3.00 |
| PIB/PB mix | 71.00 | 68.00 | 65.00 | 68.00 | 66.50 |
| Acid-Base Ratio (Molar) | 2.27:1 | 2.27:1 | 2.27:1 | 3.25:1 | 5.69:1 |

Notwithstanding the appended clauses, the disclosure set forth herein is also defined by the following clauses:
1. An extended transdermal delivery device, the device comprising:
   a buprenorphine composition formulated to deliver buprenorphine to a subject for seven days or longer, the buprenorphine composition comprising:
   buprenorphine;
   an α-hydroxy acid; and
   a pressure sensitive adhesive; and
   a backing layer.
2. The extended transdermal delivery device according to clause 1, wherein buprenorphine is buprenorphine free base.
3. The extended transdermal delivery device according to any of clauses 1-2, wherein the α-hydroxy acid is selected from the group consisting of glycolic acid, lactic acid, tartaric acid, citric acid, malic acid and mandelic acid.
4. The extended transdermal delivery device according to clause 3, wherein the α-hydroxy acid is lactic acid.
5. The extended transdermal delivery device according to any of clauses 1-4, wherein the pressure sensitive adhesive comprises a vinyl polymer.
6. The extended transdermal delivery device according to clause 5, wherein the vinyl polymer is selected from the group consisting of polyethylene, polypropylene, polyisobutylene, polybutene, polystyrene, polyvinyl chloride, polyvinyl acetate, polyvinyl alcohol and silicone.
7. The extended transdermal delivery device according to any of clauses 1-4, wherein the pressure sensitive adhesive is an acrylic polymer, acrylate copolymer or polyacrylonitrile.

8. The extended transdermal delivery device according to clause 7, wherein the pressure sensitive adhesive is an acrylate-vinyl acetate copolymer.

9. The extended transdermal delivery device according to clause 7, wherein the pressure sensitive adhesive is substantially the same as or is selected from the group consisting of DuroTak® 87-200A, DuroTak®87-2353, DuroTak®87-2100, DuroTak®87-2051, DuroTak®87-2052, DuroTak®87-2194, DuroTak®87-2677, DuroTak®87-201A, DuroTak®87-2979, and DuroTak®87-2074.

10. The extended transdermal delivery device according to any of clauses 1-9, wherein the buprenorphine composition further comprises a fatty acid ester.

11. The extended transdermal delivery device according to clause 10, wherein the fatty acid ester is selected from the group consisting of lauryl lactate, olelyl oleate and glyceryl monoleate.

12. The extended transdermal delivery device according to any of clauses 1-11, wherein the buprenorphine composition further comprises a hydrophilic polymer.

13. The extended transdermal delivery device according to clause 12, wherein the hydrophilic polymer is a polyvinylpyrrolidone polymer or copolymer.

14. The extended transdermal delivery device according to clause 13, wherein the polyvinylpyrrolidone polymer is substantially the same as or is PVP K90.

15. The extended transdermal delivery device according to clause 12, wherein the hydrophilic polymer is crosslinked.

16. The extended transdermal delivery device according to any of clauses 1-15, wherein the buprenorphine composition further comprises water.

17. The extended transdermal delivery device according to any of clauses 1-16, wherein the buprenorphine composition is a liquid or gel.

18. The extended transdermal delivery device according to any of clauses 1-17, wherein the amount of α-hydroxy acid in the composition is 5% w/w or less.

19. The extended transdermal delivery device according to any of clauses 1-18, wherein the amount of buprenorphine in the composition ranges from 2% to 15% w/w.

20. The extended transdermal delivery device according to any of clauses 1-18, wherein the amount of buprenorphine in the composition is 10% w/w or less.

21. The extended transdermal delivery device according to any of clauses 1-20, wherein the molar ratio of α-hydroxy acid to buprenorphine free base is 2 or greater.

22. The extended transdermal delivery device according to any of clauses 1-20, wherein the molar ratio of α-hydroxy acid to buprenorphine free base is 5 or greater.

23. The extended transdermal delivery device according to any one of clauses 1-22, wherein the transdermal delivery device is configured to maintain a transdermal buprenorphine flux after seven days which is within 75% or more of its peak transdermal buprenorphine flux.

24. The extended transdermal delivery device according to clause 23, wherein the transdermal delivery device is configured to maintain a transdermal buprenorphine flux after seven days which is within 90% or more of its peak transdermal buprenorphine flux.

25. The extended transdermal delivery device according to any of clauses 1-24, wherein the transdermal delivery device is configured to deliver 90% or more of the buprenorphine over the course of seven days or longer.

26. The extended transdermal delivery device according to any of clauses 1-25, wherein the transdermal delivery device is configured to provide a peak transdermal buprenorphine flux of 1.5 μg/cm$^2$/hr or greater.

27. The extended transdermal delivery device according to clause 26, wherein the transdermal delivery device is configured to provide a peak transdermal buprenorphine flux of 2.0 μg/cm$^2$/hr or greater.

28. The extended transdermal delivery device according to any of clauses 1-27, wherein the average cumulative amount of buprenorphine increases substantially linearly over the course of 7 days.

29. The extended transdermal delivery device according to any of clauses 1-22, wherein the transdermal delivery device is configured to deliver 90% or more of the buprenorphine over the course of seven days or longer when the composition comprises 10% w/w or less buprenorphine.

30. The extended transdermal delivery device according to any of clauses 1-22, wherein the transdermal delivery device is configured to deliver 90% or more of the buprenorphine over the course of seven days or longer when the molar ratio of α-hydroxy acid to buprenorphine ratio is 2 or greater.

31. The extended transdermal delivery device according to any of clauses 1-22, wherein the transdermal delivery device is configured to provide a peak transdermal buprenorphine flux of 1.5 μg/cm$^2$/hr or greater when the composition comprises 10% w/w or less buprenorphine.

32. The extended transdermal delivery device according to any of clauses 1-22, wherein the transdermal delivery device is configured to provide a peak transdermal buprenorphine flux of 1.5 μg/cm$^2$/hr or greater when the molar ratio of α-hydroxy acid to buprenorphine ratio is 2 or greater.

33. The extended transdermal delivery device according to any of clauses 1-22, wherein the transdermal delivery device is configured to deliver an average cumulative amount of buprenorphine of 60 μg/cm$^2$ or greater over the course of 7 days when the composition comprises 10% w/w or less buprenorphine.

34. The extended transdermal delivery device according to any of clauses 1-22, wherein the transdermal delivery device is configured to deliver an average cumulative amount of buprenorphine of 60 μg/cm$^2$ or greater over the course of 7 days when the molar ratio of α-hydroxy acid to buprenorphine ratio is 2 or greater.

35. The extended transdermal delivery device according to any of clauses 1-22, wherein the transdermal delivery device is configured to provide a peak transdermal buprenorphine flux of 2.0 μg/cm$^2$/hr or greater when the composition comprises 10% w/w or less buprenorphine.

36. The extended transdermal delivery device according to any of clauses 1-22, wherein the transdermal delivery device is configured to provide a peak transdermal buprenorphine flux of 2.0 μg/cm$^2$/hr or greater when the molar ratio of α-hydroxy acid to buprenorphine ratio is 2 or greater.

37. An extended transdermal delivery device comprising:
   a buprenorphine composition formulated to deliver buprenorphine to a subject for seven-days or longer, the buprenorphine composition comprising an amount of buprenorphine and an α-hydroxy acid, wherein the molar ratio of α-hydroxy acid to buprenorphine is 2 or greater; and
   a backing layer.

38. The extended transdermal delivery device according to clause 37, wherein the molar ratio of α-hydroxy acid to buprenorphine free base is 5 or greater.

39. The extended transdermal delivery device according to any of clauses 37-38, wherein buprenorphine is buprenorphine free base.

40. The extended transdermal delivery device according to any of clauses 37-39, wherein the α-hydroxy acid is selected from the group consisting of glycolic acid, lactic acid, tartaric acid, citric acid, malic acid and mandelic acid.

41. The extended transdermal delivery device according to clause 40, wherein the α-hydroxy acid is lactic acid.

42. The extended transdermal delivery device according to clauses 37-41, further comprising a pressure sensitive adhesive.

43. The extended transdermal delivery device according to clause 42, wherein the pressure sensitive adhesive comprises a vinyl polymer.

44. The extended transdermal delivery device according to clause 43, wherein the vinyl polymer is selected from the group consisting of polyethylene, polypropylene, polyisobutylene, polybutene, polystyrene, polyvinyl chloride, polyvinyl acetate, polyvinyl alcohol and silicone.

45. The extended transdermal delivery device according to clause 42, wherein the pressure sensitive adhesive is an acrylic polymer, acrylate copolymer or polyacrylonitrile.

46. The extended transdermal delivery device according to clause 45, wherein the pressure sensitive adhesive is an acrylate-vinyl acetate copolymer.

47. The extended transdermal delivery device according to clause 42, wherein the pressure sensitive adhesive is substantially the same as or is selected from the group consisting of DuroTak® 87-200A, DuroTak®87-2353, DuroTak®87-2100, DuroTak®87-2051, DuroTak®87-2052, DuroTak®87-2194, DuroTak®87-2677, DuroTak®87-201A, DuroTak®87-2979, and DuroTak®87-2074.

48. The extended transdermal delivery device according to any of clauses 37-47, wherein the buprenorphine composition further comprises a fatty acid ester.

49. The extended transdermal delivery device according to clause 48, wherein the fatty acid ester is selected from the group consisting of lauryl lactate, olelyl oleate and glyceryl monoleate.

50. The extended transdermal delivery device according to any of clauses 37-49, wherein the buprenorphine composition further comprises a hydrophilic polymer.

51. The extended transdermal delivery device according to clause 50, wherein the hydrophilic polymer is a polyvinylpyrrolidone polymer or copolymer.

52. The extended transdermal delivery device according to clause 51, wherein the polyvinylpyrrolidone polymer is substantially the same as or is PVP K90.

53. The extended transdermal delivery device according to any of clauses 50-52, wherein the hydrophilic polymer is crosslinked.

54. The extended transdermal delivery device according to any of clauses 37-53, wherein the buprenorphine composition further comprises water.

55. The extended transdermal delivery device according to any of clauses 37-54, wherein the buprenorphine composition is a liquid or gel.

56. The extended transdermal delivery device according to any of clauses 37-55, wherein the amount of α-hydroxy acid in the composition is 5% w/w or less.

57. The extended transdermal delivery device according to any of clauses 37-55, wherein the amount of α-hydroxy acid in the composition is 2% w/w or less.

58. The extended transdermal delivery device according to any of clauses 37-55, wherein the amount of buprenorphine in the composition ranges from 2% to 15% w/w.

59. The extended transdermal delivery device according to any of clauses 37-55, wherein the amount of buprenorphine in the composition is 10% w/w or less.

60. The extended transdermal delivery device according to any of clauses 37-59, wherein the transdermal delivery device is configured to maintain a transdermal buprenorphine flux after seven days which is within at least 90% of peak transdermal buprenorphine flux.

61. The extended transdermal delivery device according to any of clauses 37-60, wherein the transdermal delivery device is configured to deliver 90% or more of the buprenorphine over the course of seven days or longer.

62. The extended transdermal delivery device according to any of clauses 37-61, wherein the transdermal delivery device is configured to provide a peak transdermal buprenorphine flux of 1.5 µg/cm$^2$/hr or greater.

63. The extended transdermal delivery device according to clause 62, wherein the transdermal delivery device is configured to provide a peak transdermal buprenorphine flux of 2.0 µg/cm$^2$/hr or greater.

64. The extended transdermal delivery device according to any of clauses 37-63, wherein the transdermal delivery device is configured to deliver the average cumulative amount of buprenorphine substantially linearly over the course of 7 days.

65. The extended transdermal delivery device according to any of clauses 37-55, wherein the transdermal delivery device is configured to deliver 90% or more of the buprenorphine over the course of seven days or longer when the composition comprises 10% w/w or less buprenorphine.

66. The extended transdermal delivery device according to any of clauses 37-55, wherein the transdermal delivery device is configured to deliver 90% or more of the buprenorphine over the course of seven days or longer when the molar ratio of α-hydroxy acid to buprenorphine ratio is 2 or greater.

67. The extended transdermal delivery device according to any of clauses 37-55, wherein the transdermal delivery device is configured to provide constant transdermal buprenorphine flux after 2 days.

68. The extended transdermal delivery device according to any of clauses 37-55, wherein the transdermal delivery device is configured to provide a peak transdermal buprenorphine flux of 1.5 µg/cm$^2$/hr or greater when the molar ratio of α-hydroxy acid to buprenorphine ratio is 5 or greater.

69. The extended transdermal delivery device according to any of clauses 37-55, wherein the transdermal delivery device is configured to provide a peak transdermal buprenorphine flux of 1.5 µg/cm$^2$/hr or greater when the composition comprises 10% w/w or less buprenorphine.

70. The extended transdermal delivery device according to any of clauses 37-55, wherein the transdermal delivery device is configured to deliver an average cumulative amount of buprenorphine of 60 µg/cm$^2$ or greater over the course of 7 days.

71. The extended transdermal delivery device according to any of clauses 37-55, wherein the transdermal delivery device is configured to deliver an average cumulative amount of buprenorphine of 60 µg/cm$^2$ or greater over the course of 7 days when the composition comprises 10% w/w or less buprenorphine.

72. The extended transdermal delivery device according to any of clauses 37-55, wherein the transdermal delivery device is configured to provide a peak transdermal buprenorphine flux of 2.0 µg/cm$^2$/hr or greater when the composition comprises 10% w/w or less buprenorphine.

73. The extended transdermal delivery device according to clause 37, wherein the transdermal delivery device is configured to provide a peak transdermal buprenorphine flux of 2.0 µg/cm$^2$/hr or greater when the molar ratio of α-hydroxy acid to buprenorphine ratio is 2 or greater.

74. A method comprising:
applying to a skin surface of a subject an extended transdermal delivery device comprising:
a buprenorphine composition formulated to deliver buprenorphine to a subject for seven days or longer, the buprenorphine composition comprising:
buprenorphine;
an α-hydroxy acid; and
a pressure sensitive adhesive; and
a backing layer;
in a manner sufficient to deliver buprenorphine to the subject over an extended period of time.

75. The method according to clause 74, wherein the extended period of time is 7 days or longer.

76. The method according to any of clauses 74-75, wherein buprenorphine is buprenorphine free base.

77. The method according to any of clauses 74-76, wherein the α-hydroxy acid is selected from the group consisting of glycolic acid, lactic acid, tartaric acid, citric acid, malic acid and mandelic acid.

78. The method according to clause 77, wherein the α-hydroxy acid is lactic acid.

79. The method according to any of clauses 74-78, wherein the pressure sensitive adhesive comprises a vinyl polymer.

80. The method according to clause 79, wherein the vinyl polymer is selected from the group consisting of polyethylene, polypropylene, polyisobutylene, polybutene, polystyrene, polyvinyl chloride, polyvinyl acetate, polyvinyl alcohol, and silicone.

81. The method according to any of clauses 74-78, wherein the pressure sensitive adhesive is an acrylic polymer, acrylate copolymer or polyacrylonitrile.

82. The method according to clause 81, wherein the pressure sensitive adhesive is an acrylate-vinyl acetate copolymer.

83. The method according to clause 81, wherein the pressure sensitive adhesive is substantially the same as or is selected from the group consisting of DuroTak® 87-200A, DuroTak®87-2353, DuroTak®87-2100, DuroTak®87-2051, DuroTak®87-2052, DuroTak®87-2194, DuroTak®87-2677, DuroTak®87-201A, DuroTak®87-2979, and DuroTak®87-2074.

84. The method according to any of clauses 74-83, wherein the buprenorphine composition further comprises a fatty acid ester.

85. The method according to clause 84, wherein the fatty acid ester is selected from the group consisting of lauryl lactate, olelyl oleate and glyceryl monoleate.

86. The method according to any of clauses 74-85, wherein the buprenorphine composition further comprises a hydrophilic polymer.

87. The method according to clause 86, wherein the hydrophilic polymer is a polyvinylpyrrolidone polymer or copolymer.

88. The method according to clause 87, wherein the polyvinylpyrrolidone polymer is substantially the same as or is PVP K90.

89. The method according to any of clauses 86-88, wherein the hydrophilic polymer is crosslinked.

90. The method according to any of clauses 74-89, wherein the buprenorphine composition further comprises water.

91. The method according to any of clauses 74-90, wherein the buprenorphine composition is a liquid or gel.

92. The method according to any of clauses 74-91, wherein the molar ratio of α-hydroxy acid to buprenorphine free base is 2 or greater.

93. The method according to any of clauses 74-91, wherein the molar ratio of α-hydroxy acid to buprenorphine free base is 5 or greater.

94. The method according to any of clauses 74-91, wherein the amount of α-hydroxy acid in the composition is 5% w/w or less.

95. The method according to any of clauses 74-91, wherein the amount of buprenorphine in the composition ranges from 2% to 15% w/w.

96. The method according to any of clauses 74-91, wherein the amount of buprenorphine in the composition is 10% w/w or less.

97. A kit comprising:
two or more extended transdermal delivery devices, wherein each extended transdermal delivery device comprises:
a buprenorphine composition formulated to deliver buprenorphine to a subject for seven days or longer, the buprenorphine composition comprising:
buprenorphine;
an α-hydroxy acid; and
a pressure sensitive adhesive; and
a backing layer.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. An extended transdermal delivery device, the device comprising:
a buprenorphine composition formulated to deliver buprenorphine to a subject at a transdermal buprenorphine flux maintained at 75% or more of its peak transdermal buprenorphine flux for seven days or longer, the buprenorphine composition comprising:
buprenorphine free base in an amount from 2% to 15% w/w;
an α-hydroxy acid in an amount that is 50% or less by weight of the buprenorphine;
a permeation enhancer; and a pressure sensitive adhesive; and a backing layer,
wherein the α-hydroxy acid is lactic acid and the permeation enhancer is lauryl lactate.

2. The extended transdermal delivery device according to claim 1, wherein the molar ratio of α-hydroxy acid to buprenorphine free base is 2 or greater.

3. The extended transdermal delivery device according to claim 1, wherein the amount of α-hydroxy acid in the composition is 5% w/w or less.

4. The extended transdermal delivery device according to claim 1, wherein the pressure sensitive adhesive comprises a vinyl polymer.

5. The extended transdermal delivery device according to claim 1, wherein the pressure sensitive adhesive is an acrylic polymer, acrylate copolymer or polyacrylonitrile.

6. The extended transdermal delivery device according to claim 5, wherein the pressure sensitive adhesive is an acrylate-vinyl acetate copolymer.

7. The extended transdermal delivery device according to claim 1, wherein the transdermal delivery device delivers 90% or more of the buprenorphine to the subject over the course of seven days or longer.

8. The extended transdermal delivery device according to claim 1, wherein the buprenorphine composition further comprises water.

9. The extended transdermal delivery device according to claim 8, wherein the buprenorphine composition is a liquid or gel.

10. An extended transdermal delivery device comprising:
a buprenorphine composition formulated to deliver buprenorphine to a subject at a transdermal buprenorphine flux maintained at 75% or more of its peak transdermal buprenorphine flux for seven-days or longer, the buprenorphine composition comprising:
buprenorphine free base in an amount from 2% to 15% w/w;
an α-hydroxy acid in an amount that is 50% or less by weight of the buprenorphine; and
a permeation enhancer,
wherein the α-hydroxy acid is lactic acid and the permeation enhancer is lauryl lactate, and
wherein the molar ratio of α-hydroxy acid to buprenorphine is 2 or greater; and a backing layer.

11. The extended transdermal delivery device according to claim 10, wherein the buprenorphine composition is a liquid or gel.

12. The extended transdermal delivery device according to claim 1, wherein pressure sensitive adhesive comprises polyisobutylene and polybutene.

13. The extended transdermal delivery device according to claim 10, further comprising a pressure sensitive adhesive that comprises polyisobutylene and polybutene.

* * * * *